(12) United States Patent
Dillon et al.

(10) Patent No.: US 9,087,295 B1
(45) Date of Patent: Jul. 21, 2015

(54) DETERMINATION OF SEQUENCE FREQUENCY

(71) Applicant: The United States of America as represented by the Secretary of the Navy, Washington, DC (US)

(72) Inventors: Brian S. Dillon, King George, VA (US); Jeremy Gene Kelly, Fredericksburg, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 263 days.

(21) Appl. No.: 13/783,639

(22) Filed: Mar. 4, 2013

(51) Int. Cl.
*G06N 5/02* (2006.01)

(52) U.S. Cl.
CPC ..................................... *G06N 5/02* (2013.01)

(58) Field of Classification Search
None
See application file for complete search history.

(56) References Cited

U.S. PATENT DOCUMENTS

| | | | |
|---|---|---|---|
| 8,112,504 B2 | 2/2012 | Logan et al. | 709/219 |
| 8,321,465 B2 | 11/2012 | Farber et al. | 707/802 |
| 8,655,908 B2 | 2/2014 | Kenedy et al. | 707/769 |
| 2007/0244951 A1* | 10/2007 | Gressel et al. | 708/252 |
| 2014/0228223 A1* | 8/2014 | Gnirke et al. | 506/2 |

OTHER PUBLICATIONS

Su et al., A Prediction System for Web Requests using N-gram Sequence Models, 2000, IEEE, pp. 214-221.*
Sheng-Lan, Optimal Hash List for Word Frequency Analysis, 2010, IEEE, pp. 242-245.*
J. Berstel et al.: "The origins and combinatorics on words", *Euro. J. of Combinatorics* 28 996-1022 (2007). http://www-igm.univ-mlv.fr/~berstel/Articles/2007Origins.pdf.
N. G. deBruijn, "A combinatorial problem", *Proc. Koninklijke Nederlandse Akademie v. Wetenschappen* 49, 758-764(1946) http://www.dwc.knaw.nl/DL/publications/PU00018235.pdf.
G. Hurlbert et al., "On the de Bruijn Torus Problem", J. of Combinatorial Theory A 64 (1) 50-62 (1993). https://math.la.asu.edu/~hurlbert/papers/DBTP.pdf http://www.cs.dartmouth.edu/reports/TR92-181.pdf.
M. H. Martin "A problem in arrangements", Bull. of the American Mathematical Society 40 (12) 859-864. http://www.ams.org/journals/bull/1934-40- 12/S0002-9904-1934-05988-3/S0002-9904-1934-05988-3. pdf.
J. Baker, "De Bruijn graphs and their applications to Fault Tolerances", Oregon State University (2011). http://www.math.oregonstate.edu/~swisherh/JoelBaker.pdf http://ir.library.oregonstate.edu/xmlui/bitstream/handle/1957/26215/De%20Bruijn%20graphs%20and%20their%20applications%20to-%20fault%20tolerant%20networks.pdf?sequence=1.

* cited by examiner

*Primary Examiner* — Alan Chen
(74) *Attorney, Agent, or Firm* — Gerhard W. Thielman, Esq

(57) ABSTRACT

A computer-implemented sequence analysis process is provided for determining frequency in an n-gram hash sequence of a symbolic string, such as a series of characters. The method includes initializing a hash table, creating a matrix, reading the present value in the sequence, determining whether the present value is unknown, inserting a value index into the hash table if unknown and identifying the value index otherwise, and incrementing a cell within the array. The hash table has a plurality of levels from one to n. The matrix includes first and second indices corresponding to an array of cells. The first index corresponds to an end of a prior value, while the second index corresponds to a start of a present value. The cell corresponds to the first index for the prior value and the second index for the present value.

8 Claims, 22 Drawing Sheets

```
1   MAX_LENGTH = 10; //largest n - gram size; set by parameter to this process       ⎫
2   TABLE_START = 15; //starting dimension of table; also set by parameter to this process  ⎬ 1410

//create hash tables, variables and matrices for all levels                      ⎫
5   int [][][] matrices = new [MAX_LENGTH][TABLE_START][TABLE_START];
6   Hashtable<String, Integer> [] indices = new Hashtable<String, Integer>[MAX_LENGTH];  ⎬ 1420
7   int [] number = new int[MAX_LENGTH];
8   int [] last = new int[MAX_LENGTH];
9   boolean [] active = new boolean[MAX_LENGTH];                                     ⎭

//sequence processing loop
12  while(intputStream.hasNext())
    {
14      String value = inputStream.next();//next value in the sequence //loop through all layers
17      for(i=1 to MAX_LENGTH)
        {
19          if(!indices.hasKey(value))//this is a new value never seen before
            {
21              if(number[i]==matrices[i].length)//table has reached maximum size
                {
                    //enlarge table before continuing
24                  int k = number[i];//size of current matrix
25                  int [][] temp = new int[k*2][k*2];
26                  copyTable(matrices[i],temp);//O(k^2) copy based on matrix size
27                  matrices[i] = temp;//store new table in set of matrices
                }
30              indices[i].put(value,number[i]++);//add new value with associated index
            }
33          int index = indices[i].get(value);//index of latest value 35          if(!active[i])//inactive tables are actived by the first value
            {
37              active[i]=true;//avoid this loop hereafter
38              last[i] = index;//remember last used index
39              break;//abort for loop; do not process higher layers
            }
41          else // active tables process values
            {
43              matrices[i][last[i]][index]++;//increment count
44              value = join(last[i],index);//joining process can be index or value based
45              last[i] = index;//remember last used index
            }
        }
    }
```

Fig. 14

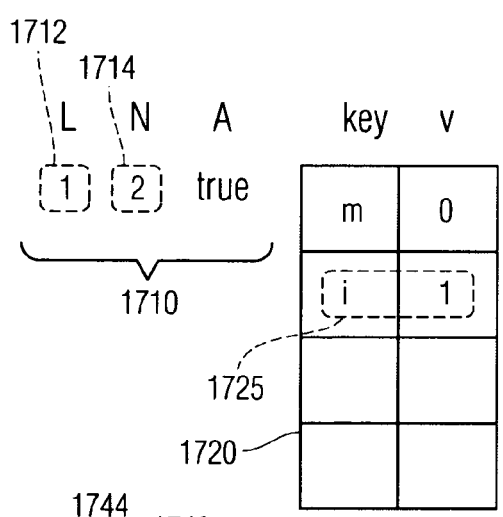
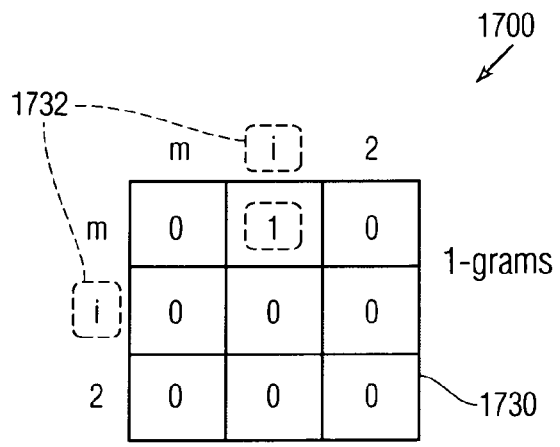
Fig. 17A
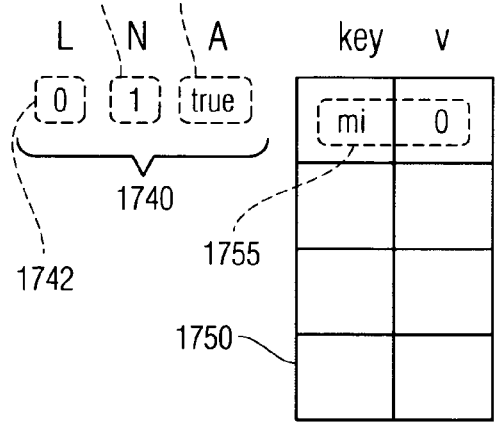
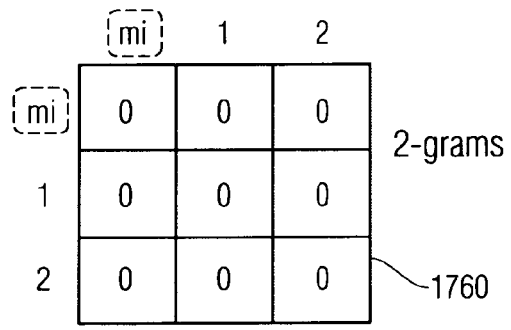
Fig. 17B
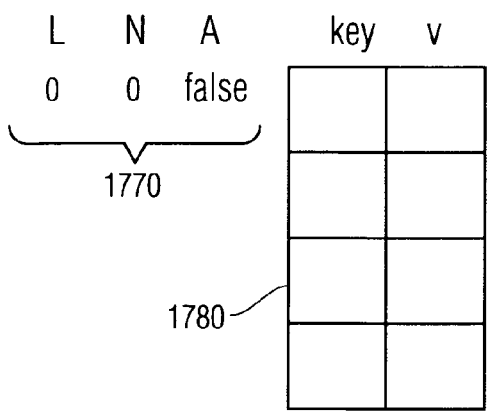
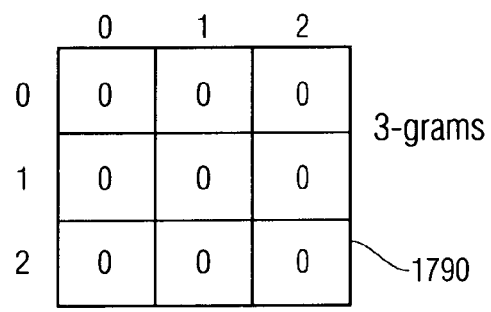
Fig. 17C

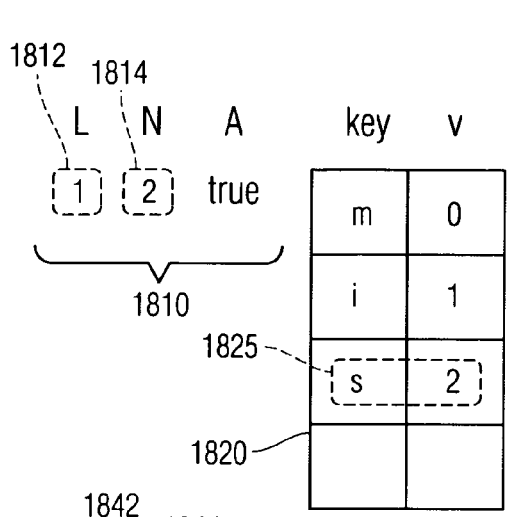
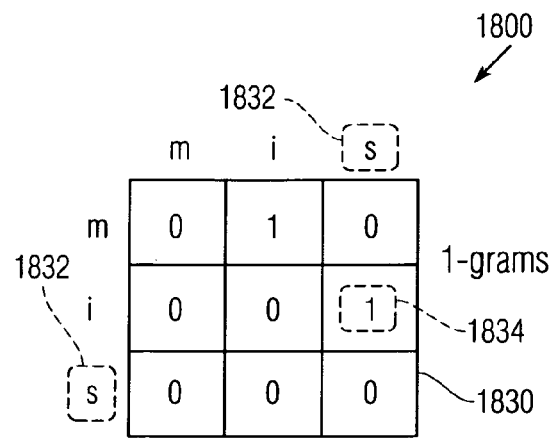
Fig. 18A
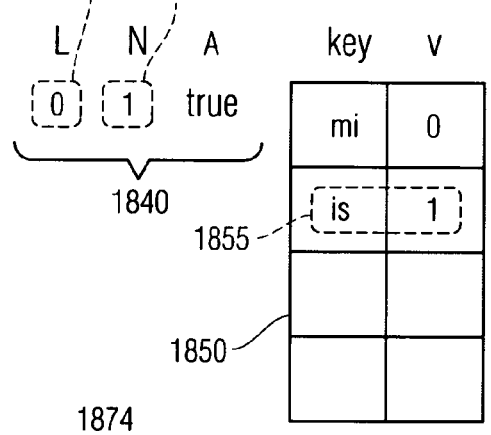
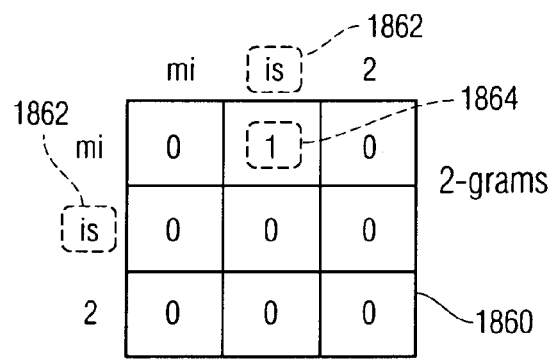
Fig. 18B
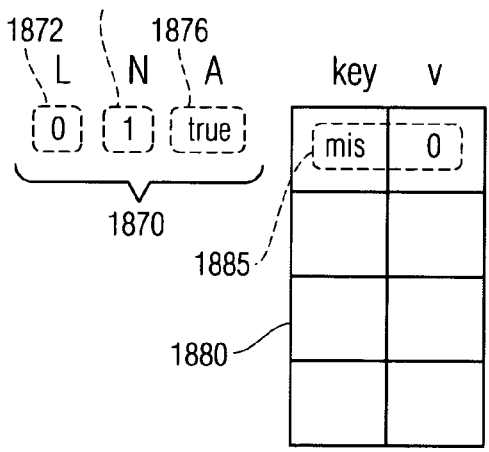
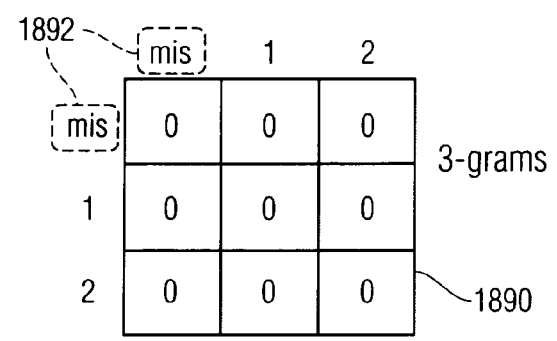
Fig. 18C

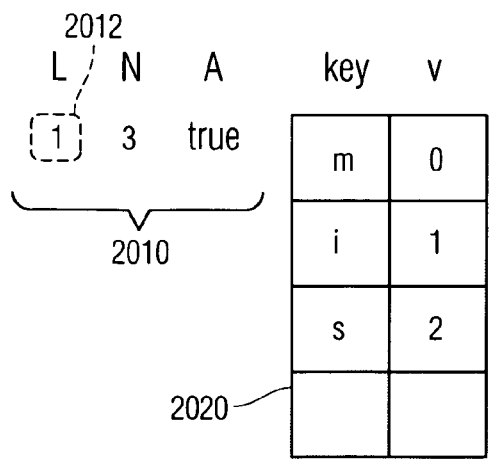
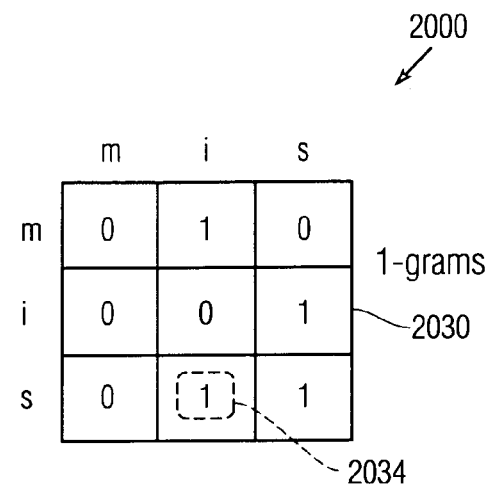
Fig. 20A
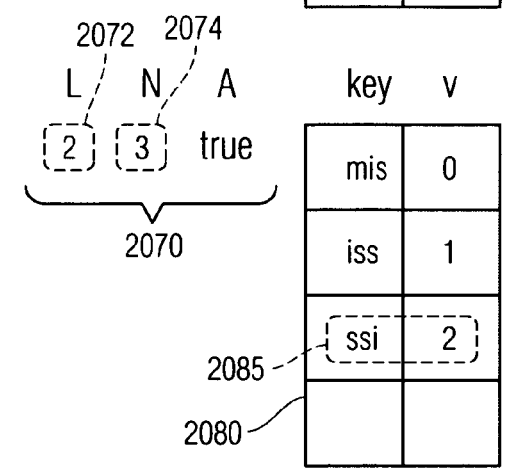
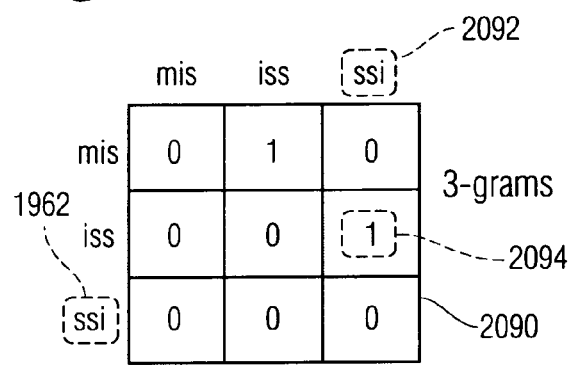
Fig. 20C
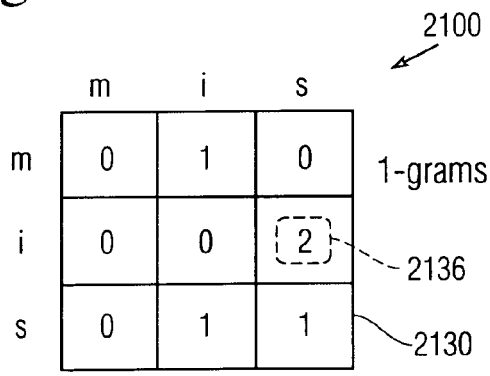
Fig. 21A Table of 1-grams                                    2300

|     | m | i | s | p |
| --- | - | - | - | - |
| m   | 0 | 1 | 0 | 0 |
| i   | 0 | 0 | 2 | 1 |
| s   | 0 | 2 | 2 | 0 |
| p   | 0 | 1 | 0 | 1 |

Table of 2-grams

|    | mi | is | ss | si | ip | pp | pi |
| -- | -- | -- | -- | -- | -- | -- | -- |
| mi | 0  | 1  | 0  | 0  | 0  | 0  | 0  |
| is | 0  | 0  | 2  | 0  | 0  | 0  | 0  |
| ss | 0  | 0  | 0  | 2  | 0  | 0  | 0  |
| si | 0  | 1  | 0  | 0  | 1  | 0  | 0  |
| ip | 0  | 0  | 0  | 0  | 0  | 1  | 0  |
| pp | 0  | 0  | 0  | 0  | 0  | 0  | 1  |
| pi | 0  | 0  | 0  | 0  | 0  | 0  | 0  |

Table of 3-grams

|     | mis | iss | ssi | sis | sip | ipp | ppi |
| --- | --- | --- | --- | --- | --- | --- | --- |
| mis | 0   | 1   | 0   | 0   | 0   | 0   | 0   |
| iss | 0   | 0   | 2   | 0   | 0   | 0   | 0   |
| ssi | 0   | 0   | 0   | 1   | 1   | 0   | 0   |
| sis | 0   | 1   | 0   | 0   | 0   | 0   | 0   |
| sip | 0   | 0   | 0   | 0   | 0   | 1   | 0   |
| ipp | 0   | 0   | 0   | 0   | 0   | 0   | 1   |
| ppi | 0   | 0   | 0   | 0   | 0   | 0   | 0   |

DETERMINATION OF SEQUENCE FREQUENCY

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to determining n-gram frequency in a sequence. In particular, the invention relates to counting sequences of characters based on the de Bruijn graph.

The problem of counting frequency for n-grams in a sequence is routine in text mining and genomic studies. However, the process for calculating the frequency is more complex in terms of time. The typical algorithm requires a single pass to enumerate all the n-grams in the sequence. For each term, the algorithm then makes a second pass to count the matching next term for each occurrence in the sequence. Such an algorithm calculates the frequency of all n-grams of length n and must be repeated for other lengths. This conventional algorithm has complexity of order $O(kn^2)$ for k sets of n-grams. Typically this algorithm is only executed a few times due to its complexity.

Conventional text miners limit themselves 1-to-5 length n-grams because further analysis is just too expensive. Among genomic researchers the solution is to chop larger sequences into smaller sizes. That kind of analysis is called "de novo". Literature in that field specifically states that de novo analysis is a work around the $O(n^2)$ complexity of the algorithm. The de novo analysis limits the size of n so that complexity does not exceed real time constraints.

SUMMARY

Conventional frequency determination techniques yield disadvantages addressed by various exemplary embodiments of the present invention. In particular, an analysis process is provided using computer-implementation for determining frequency in an n-gram hash sequence of a symbolic string. The process includes initializing a hash table, creating a matrix, reading the present value in the sequence, determining whether the present value is unknown, inserting a value index into the hash table if unknown and identifying the value index otherwise, and incrementing a cell within the array.

In various exemplary embodiments, the hash table has a plurality of levels from one to n. The matrix includes first and second indices corresponding to an array of cells. The first index corresponds to an end of a prior value, while the second index corresponds to a start of a present value. The cell corresponds to the first index for the prior value and the second index for the present value.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. 14 is a sequence view of a pseudo-code for the technique;
FIGS. 17A, 17B and 17C are tabular matrix views for a second iteration;
FIGS. 18A, 18B and 18C are tabular matrix views for a third iteration;
FIGS. 19A, 19B and 19C are tabular matrix views for a fourth iteration;
FIGS. 20A, 20B and 20C are tabular matrix views for a fifth iteration;
FIGS. 21A, 21B and 21C are tabular matrix views for a sixth iteration;
FIG. 23 is a tabular views of results from an example based on the example in the final iteration.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

In accordance with a presently preferred embodiment of the present invention, the components, process steps, and/or data structures may be implemented using various types of operating systems, computing platforms, computer programs, and/or general purpose machines. In addition, those of ordinary skill in the art will readily recognize that devices of a less general purpose nature, such as hardwired devices, or the like, may also be used without departing from the scope and spirit of the inventive concepts disclosed herewith. General purpose machines include devices that execute instruction code. A hardwired device may constitute an application specific integrated circuit (ASIC) or a field programmable gate array (FPGA) or other related component.

I. Applications and Modes of Operation:

Algorithm and accompanying data structure captures a sequence S of values (e.g., textually symbolic characters) and decomposes the sequence into a set of frequency charts depicting the frequency of occurrence for all sub-sequences n-length or smaller. Such a sub-sequence is commonly referred to as an n-gram in the field of text mining or k-gram in the field of genomic sequencing. The value n represents an integer.

For the sake of standard terminology in this application such sub-sequences shall be referred to as n-grams. Also, for the sake of standard form such sequences shall be depicted as letter characters, although such a sequence may consist of text, genetic base pairs, events, occurrences or other sequential data that might for convenience be depicted by a string of concatenated symbols. Recognizing always that an event or base pair may be represented by a letter, any string of letters would represent a generic sequence. The exemplary algorithm executes through the whole sequence of characters S in $O(|S|)$ time (i.e., order absolute sequence) and creates a set of k tables for 1-grams, 2-grams, . . . and k-grams. Each matrix table corresponds to the frequency with which one n-gram follows another to produce an (n+1)-gram. The resulting tables may be read one row or column at a time to extract frequency information.

Figure 1:
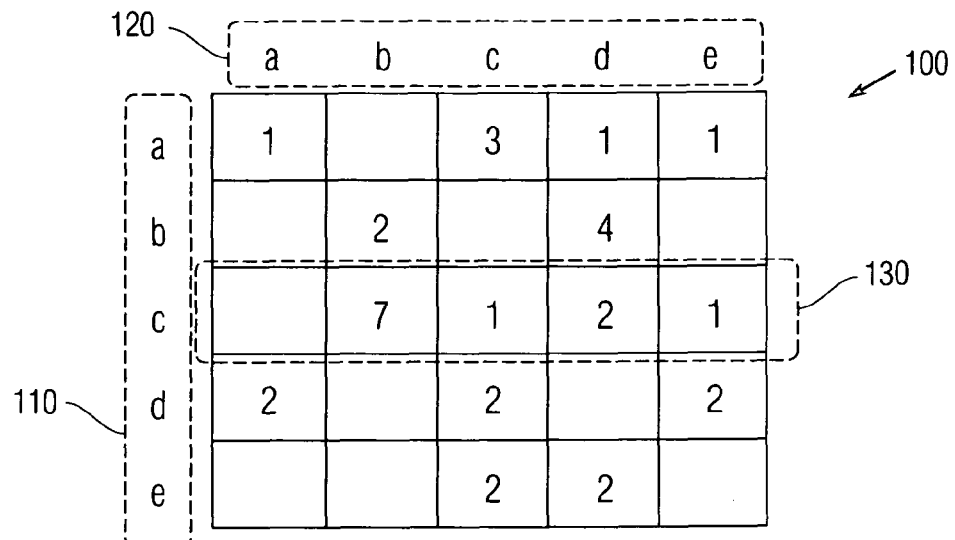
FIG. 1 is a tabular matrix view of character frequency.

Algorithm and accompanying data structure captures a sequence of values and decomposes the sequence into a set of frequency charts. Frequency analysis can then be performed on such charts as shown in FIG. 1 to determine various statistical values. FIG. 1 illustrates a matrix view 100 with indices 'a b c d e' for both rows 110 and columns 120. The number of occurrences of some n-gram can be determined by row sum. As an example, the occurrence of character 'c' in the third row 130 is the sum of (0+7+1+2+1) or 11. By contrast, the total occurrences of all the rows constitute the sum of (6+6+11+6+4) or 33. The proportional frequency of some n-gram can be determined by row sum in proportion to total n-gram frequency. As an example the proportional frequency of 'c' is 11/33 or 33%. In other embodiments additional matrices at higher orders create more complex frequency calculations.

Algorithm and accompanying data structure captures a sequence of values and decomposes the sequence into a set of frequency charts. Bayesian probabilities can be calculated from these charts to predict behaviour, determine the probability of a given input and to create a Bayesian network for other applications. Referring again to the chart shown in matrix view 100, the occurrence of 'c' is 11, but the occurrence of 'c' precedes the occurrence of 'Ca', 'cb', 'cc', 'cd' and 'ce' with various specific probabilities. Therefore one can determine that if 'c' occurs, then 'b' is the most probable (64% likely) follow-on value. By contrast, if 'ca' was to occur, such an occurrence would stand out as extremely unlikely, and thereby draw attention to a potential anomaly. In other embodiments, additional matrices at higher orders create more complex Bayesian logic, thereby enabling predictive analysis of the final n-gram based on a single 1-gram.

Due to the existence of this predictive analysis capability, anomalous sequences are easily detected. The occurrence of a sequence 'acdae' has a computable probability based on the given matrix. From the fact that 'c follows 'a' with a probability of 0.5, 'd' follows 'c' with a probability of 0.18, 'a' follows 'd' with a probability of 0.33, 'e' follows 'a' with a probability of 0.125 the probability of the sequence 'acdae' is calculated as 0.0038. By the same process, the sequence 'cbdcb' has a probability of 0.09. This would indicate that 'cbdcb' occurs twenty-three times more frequently than 'acdae', rendering the latter an anomaly.

In a static analysis mode, a sequence of known "normal" behaviour may be analyzed using the algorithm and accompanying data structure. From this one action, static analysis can calculate predictive values for normal behaviour. Using this set of normal behaviour as a baseline, a new sequence may be analyzed in order to determine the likelihood of each sub-sequence. The outcome constitutes a mapping of the complete new sequence showing where anomalies occur, their duration and when normal behaviour begins again.

Figure 2:
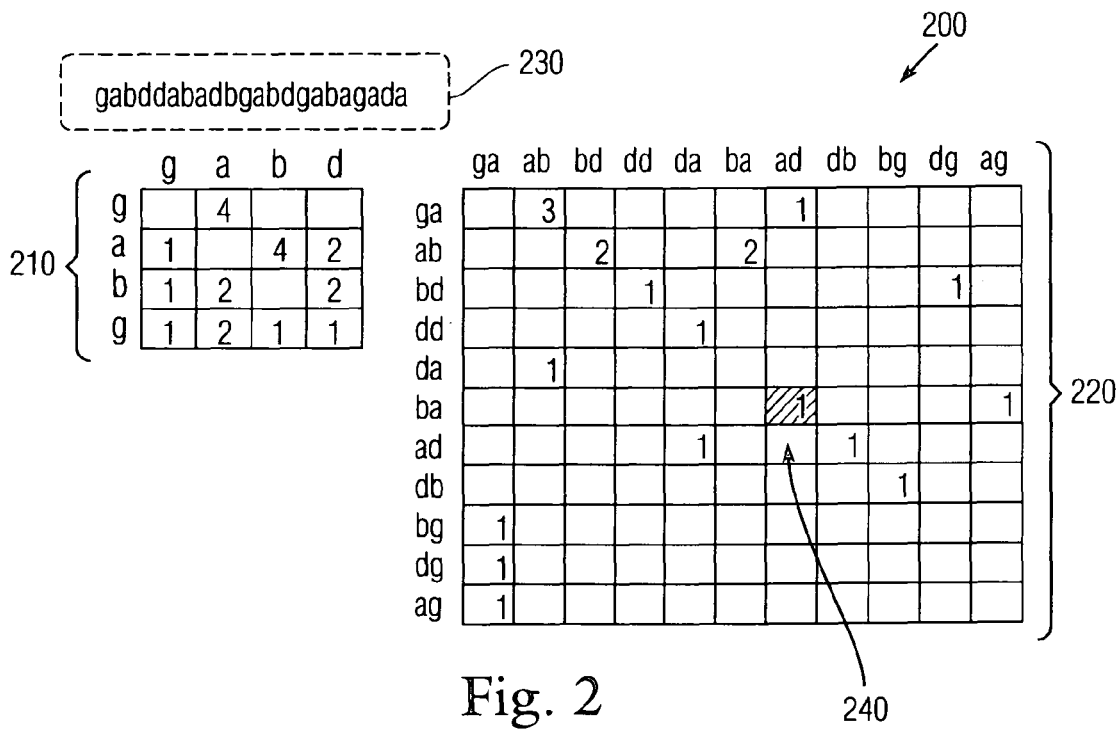
FIG. 2 is a tabular matrix view of 1-gram and 2-gram tables.

In a static analysis mode and using the predictive values to create a Bayesian net, one can create active resistance to undesirable outcomes. FIG. 2 shows matrix views 200 of a 1-gram table 210 and a 2-gram table 220 for a sequence 'gabddabadbgabdgabagada' 230. As identified by the demarcated intersection or cell 240 of row 'ba' and column 'ad', the sequence 'bad' is shown to be undesirable in the second 2-gram table 220. In the course of the sequence processing, if 'b' occurs, then there is a 40% chance of being followed by 'a'. When 'ba' occurs, there is a 50% chance of being followed by 'ad'. Thus there is a 20% chance of the undesirable outcome 'bad' simply based on the occurrence of 'b'. The system may feel that this is sufficiently low to permit the sequence to continue, but once 'ba' occurs the now 50% probability of 'bad' is unacceptable. Such analysis allows the system to actively resist undesirable outcomes. Such calculations are easily made as part of a Bayesian net and may extend to many layers of complexity beyond this simple example.

In a dynamic analysis mode a stream of events may be processed without any foreknowledge of baseline behaviour. In this mode the matrix counters continually increment with each event and on a periodic basis appropriate for that system a matrix-wide reduction may be effected. This reduction will prevent the counter from increasing without bounds and reduce or eliminate any lower-order occurrences. The appropriate timing of such a reduction may be fine tuned for the system in question in order to reduce false positives.

Figure 3:
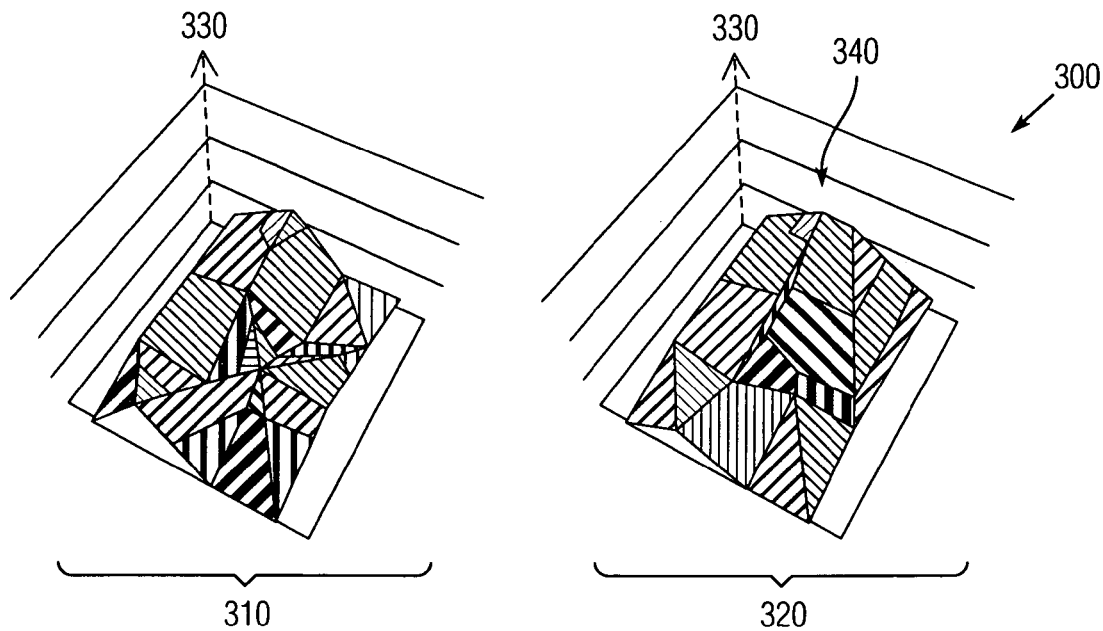
FIG. 3 is a contour graphical view of event frequency.

In a dynamic analysis mode and using the frequency chart in its current state at any point in time, one can apply the algorithmic process to detect anomalies. FIG. 3 shows perspective plot views 300 of a pair of dynamic contour graphs 310 and 320. Through a perpetual build and reduce process the normal behaviour of the system might be represented by frequency counts denoted by increasing layers as indicated by the arrows 330.

Frequent sequences are reduced so that no behaviour stands out as in the graph 310. If, however, a spike 340 in one behaviour was to occur, that would become noticeable as in the graph 320. Especially where such behaviour is seen infrequently such analysis could be automated to trigger an alarm indicating an unusual event. Moreover, the location of the spike 340 would indicate exactly which sequence of events led to the alarm.

Algorithm and accompanying data structure may be adapted for parallel processing without loss of information. In the parallel processing form P sections of a large sequence may be processed individually from 1-grams up to n-grams. The totals from the P frequency charts may be aggregated for a total value. As a final step the boundary conditions between the sections must be considered.

Figure 4:
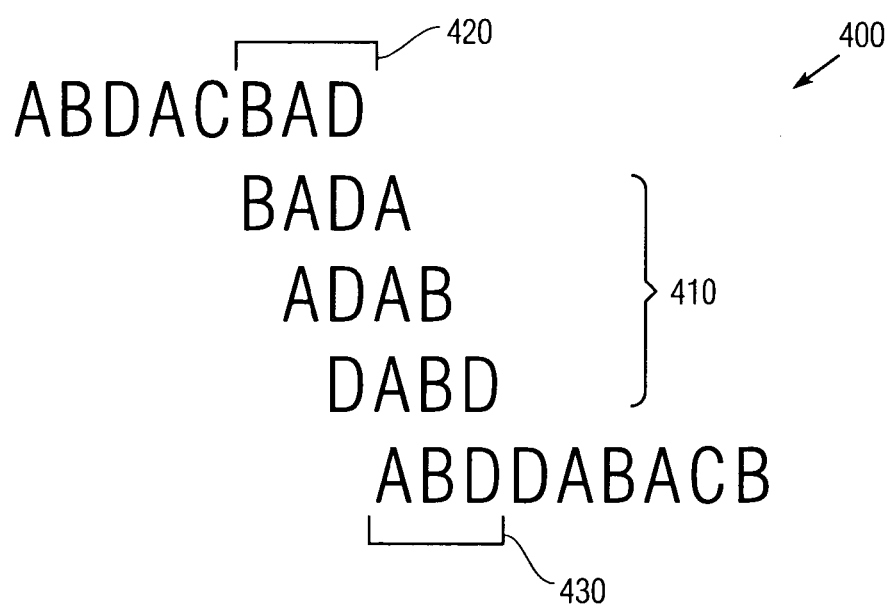
FIG. 4 is a digital view of sequences compared at their terminal ends.

Thus the last and first n−1 values must be evaluated on such boundaries as shown in FIG. 4, which shows a processing view 400 involving up to 4-gram strings 410 and so the three values on that boundary are involved in additional 4-gram 'BADA', 'ADAB' and 'DABD' that require processing. The upper sequence ends in boundary 'BAD' 420 and the lower sequence begins in boundary 'ABD' 430. Thus by parallel processing P sequences of k length can be processed in k time with an additional smaller cost involving the individual boundaries. Such a process is not dissimilar to the Map-Reduce paradigm favoured for large data sets.

Figures 5A, 5B:
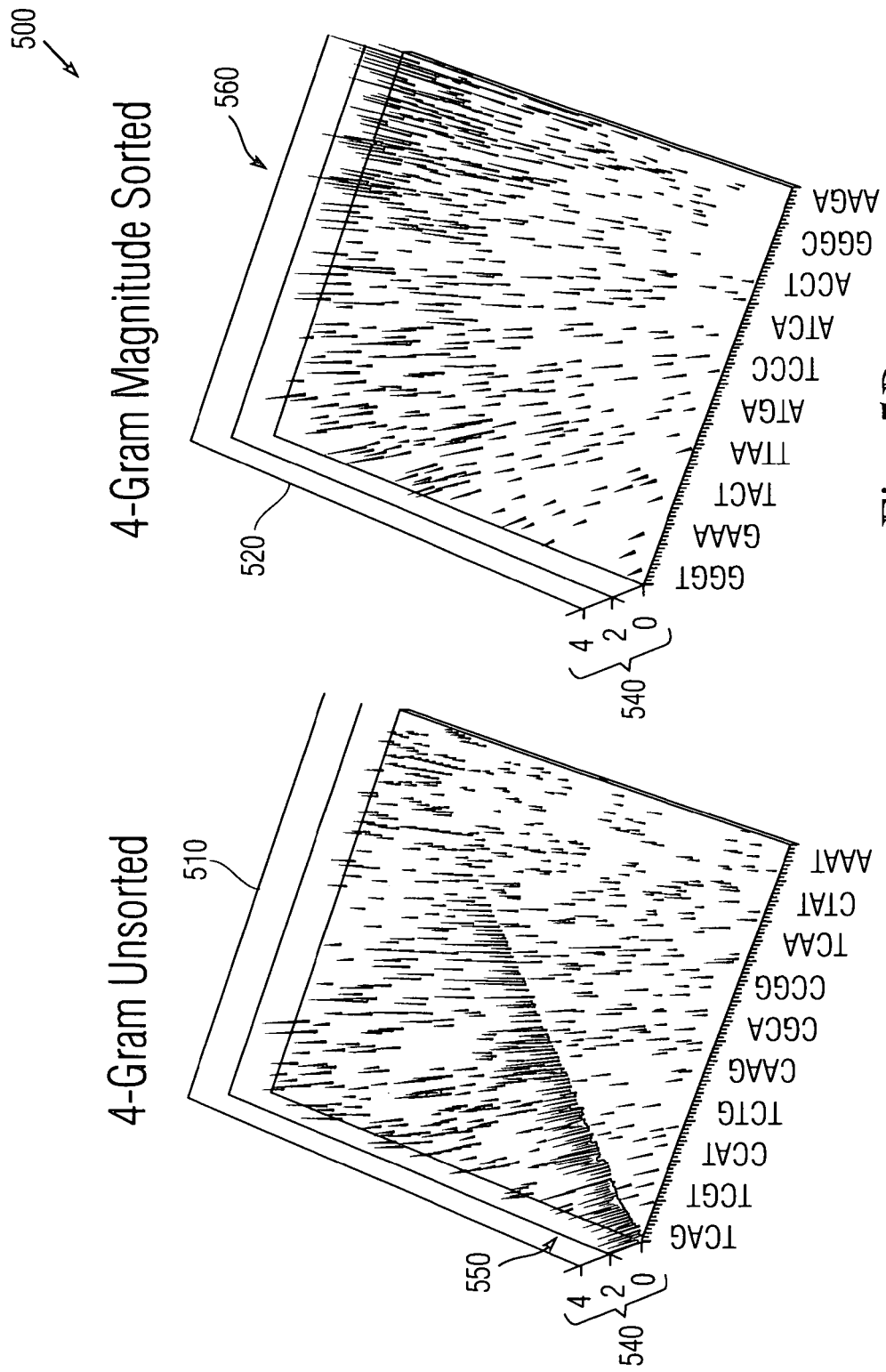
FIGS. 5A, 5B and 5C are contour graphical views of 4-gram nucleotide sorting.
Figures 5C, 6:
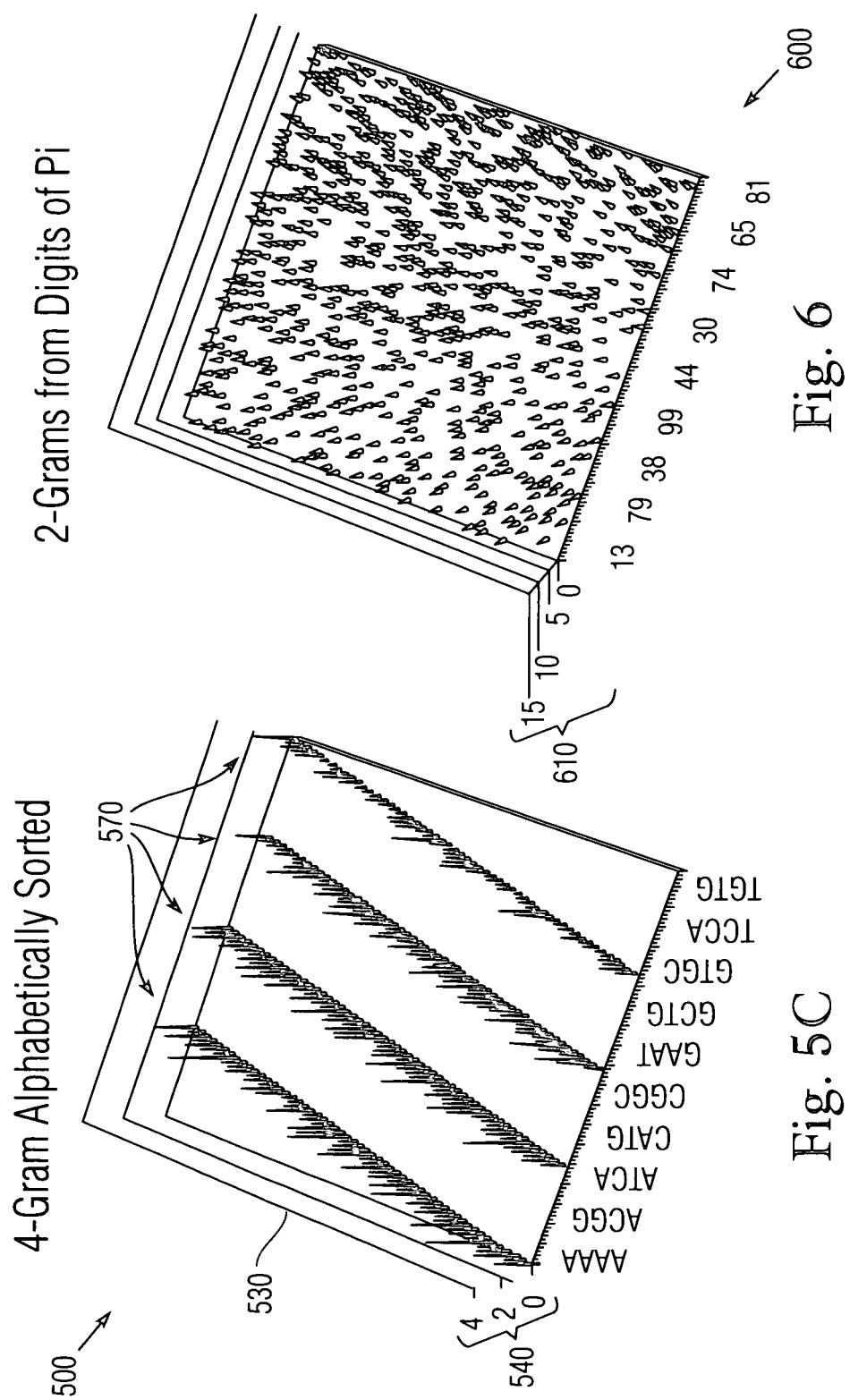
FIG. 6 is a contour graphical view of 2-gram numerical digits.

Algorithm and accompanying data structure produce output which may be used to further analyze and understand the domain. FIGS. 5A, 5B and 5C show perspective frequency graphs 500 of 4-gram for a random deoxyribo-nucleic acid (DNA) nucleotide sequence. FIG. 5A illustrates a 4-gram unsorted graph 510. FIG. 5B illustrates a 4-gram magnitude sorted graph 520. FIG. 5C illustrates a 4-gram alphabetically sorted graph 530. These nucleotides are labeled 'A' for adenine, 'T' for thymine, 'G' for guanine and 'C' for cytosine. A frequency scale 540 denotes the magnitude of the sequence occurrences, denoted by spikes rising from the base of the graphs.

As shown by the unsorted graph 520, a matrix of n-grams exhibits a diagonal line 550 that seems to indicate strong correlation of some form. This seeming correlation is in fact an artifact of the method of construction for the structure. Sorting by magnitude of row and column produces a much less predictable pattern, such as the distributed convergence 560 near the rightward edges of the magnitude sorted graph 520. This may be used to better understand the concept of frequency among n-grams. One can demonstrate that some sorting criteria expose predictable patterns of behaviour that can be quite regular. In this example, the alphabetical sorting 530 graph exposes the predictable nature of feasible n-gram joining 570. Similar techniques may be developed using large-order data to find other regularities that have greater significance in the individual domain.

II. Advantage Over Conventional Techniques:

Using the current state of the art, the process for calculating 1-grams is $O(n^2)$ or quadratic time with an $O(k)$ or linear memory requirements. The algorithm simply consists of two passes over the entire sequence. The first pass is to determine all the 1-grams found in the sequence, let's say k. The second pass starts by initializing a k-length array and then incrementing each counter as the 1-gram is encountered. Thus the algorithm is able to produce a k-length array with k-counts for k values.

This algorithm executes in quadratic time, but during that interval, the process only produces a count for one type of n-gram. In order to produce significant data sets for higher order n-grams, the conventional process must be executed repeatedly at a quadratic cost for each new n-gram set. Thus for a sequence is being analyzed for a maximum of M-grams, this process must be run M times for a total run time of $O(M \cdot n^2)$. In practice, for M>5 such analysis becomes infeasible for large values of n.

Conventional algorithms in the current state-of-the-art use only linear memory. This constitutes an advantage as conventional techniques inhibit allocation of additional memory that could be used for other purposes. Also, the output is exactly fit to the size of the data. This feature is useful in post processing where any unused additional memory would require additional processing to interpret correctly. The exact size of this memory requirement comes at a cost in reduced flexibility, which is a deficiency that exemplary embodiments remedy.

Among those in greatest need of a solution to this problem are genetic researchers who are conducting frequency counts on extremely large order sequences. In such a case, the quadratic order of the algorithm becomes a burden, and the processing of the entire sequence cannot be accomplished in reasonable time. Instead the sequence is divided into sections, which are examined individually in what is called the de novo process. This process yields correct answers, but is performed in this manner expressly for the purpose of defeating the $O(n^2)$ time requirement.

In contrast, using the exemplary algorithm and accompanying structure, the process for calculated 1-grams is $O(n)$ or linear time with an $O(k^2)$ or linear memory requirement. The algorithm operates by starting with a $k_1$-by-$k_1$ ($k_1 \times k_1$) matrix, where $k_1$ is the assumed starting size of k. As each value in the sequence is processed, the process either matches an existing value in $k_1$ or the value is added to the set. When the set exceeds the size of $k_1$, the size is doubled to $k_2$ the current matrix is copied into a new matrix of size $k_2$-by-$k_2$ ($k_2 \times k_2$) and the process continues. As a final step the exact k-by-k (k×k) matrix may be coped once more so that no excess rows or columns exist where $k_n$ is larger than k. Thus the algorithm is able to produce a sparse matrix of order k×k which contains counts for all 1-grams and 2-grams. This is the most primitive step in the algorithm.

Note that exemplary embodiments of this technique improve upon the conventional state of the art by an order of magnitude in reducing time for completion. The artisan of ordinary skill can note that the process of copying the existing matrix repeatedly is an $O(k^2)$ operation. For each increasing size of $k_n$ the previous order becomes irrelevant as the new order is larger. The cost for this operation, however, is miniscule compared with the total processing time. For exceptionally large orders of n, the overall cost is still capped by $O(n)$ so that these copy operations become trivial by comparison.

For example, take the 4-gram table of base pairs. There are $4^4$ or 256 possible 4-grams, all or some of which may exist in a large sequence. If the table starts out as 4×4, the table must be doubled in size a total of six times. The largest operation is $128^2$ or 16384 copy operations and the total number of copy operations is 21,840 or 133% of the $O(k^2)$ estimate. The 133%-of-estimate holds true for all large copy operations. If the entire sequence is as large as 25,000 base pairs the $O(n)$ processing time already exceeds the number of copy operations. In fact, the average size of single human gene is only 3,000 values, but some single genes are as large as 2.4 million base pairs and the total genome is 3.1647 billion base pairs. In a sequence of that size, the copying operations represent less than 0.0007% of the total processing costs.

Also recall that in practice the conventional state of the art is limited to 5-grams in terms of feasible calculation time. Using the exemplary algorithm and accompanying structure, one can calculate 1-grams, 2-grams, 3-grams, 4-grams and 5-grams simultaneously within $O(n)$ time. In practice, this has been found to enable higher-order analysis that has not been computationally accessible before. Presumably, this aspect of exemplary embodiments can open new vistas of high-order frequency data in the near future.

The total memory usage for this operation is order $O(k^2)$. While the doubling effect may result in a slightly larger than necessary matrix, this does not exceed $O(4k^2)$. Suppose that k is 101, and at some point the current matrix is $k_n \times k_n$ where $k_n$=100. At some point the $k^{th}$ element must be added. In such an operation results in a 200-by-200 matrix when only a 101-by-101 matrix is required. This is a 40,000:10,201 or about 4:1 ratio as stated previously and thus $O(4k^2)$. This is known to be within the same order as $O(k^2)$ according to standard computational theory and thus represents a theoretical bound on memory space. As such, this exceeds the state of the art by one order of magnitude.

Furthermore, consider that such a matrix contains frequency counts for 1-grams and 2-grams. This means that 1-grams are represented by columns and 2-grams are represented by individual matrix cells. This is a property of de Bruijn graphs, which are the basis for the accompanying structure. In the state of the art, representing the latter data set would require additional memory. Thus the apparent order of magnitude disparity is reduced when one considers the next order of data contained in the structure.

One should note however, that conventional techniques return exactly k values with no additional or excess memory being used. By contrast, exemplary embodiments with the disclosed algorithm and k×k structure contains cells for all $k^2$ 2-grams whether or not they are feasible. Infeasible 2-grams will be represented by a zero so that the structure may be a sparse matrix. In practice the sparcity of the matrix is domain specific. For example in genetics, the frequency with which any base pair is followed by any other base pair is relatively uniform so that a 1-gram matrix is unlikely to contain any zeros, much less be considered sparse. On the other side of the scale, sequences of letters in English would show no occurrences of several sequences such as 'qj' or 'xx' creating a very sparse matrix of 1-grams. In each example, the 2-gram values are represented in the $O(k^2)$ memory. Depending on the domain therefore, the matrix may be sparse. Consider therefore the best and worst case scenarios for the purpose of memory comparison.

For example, evaluation of the sequence 'abcdabcdabcd . . . ' for 2-gram frequencies can be compared using conventional and exemplary methods. The conventional technique would use only four memory slots for the final result corresponding to the four occurring 2-grams. For the same data, the exemplary process would require sixteen memory slots, only four of which would be filled with data. Thus the matrix in only 25% full and is thereby inefficient in its memory usage. Such a sequence consists of k elements in the same order and possibly repeated multiple times. Therefore depending on the set of 1-grams, this value can be even worse. The sequence above contained only five 1-grams. For the set of digits {'0', '1', '2', . . . '9'}, the minimum theoretical efficiency is 10%. For the set of all single-case characters {'a', 'b', 'c', . . . 'z'}, the minimum theoretical inefficiency is 3.8%. There is no lower bound given a sufficiently large set of 1-grams. This example represents a worst case scenario.

Suppose instead that the digits of the transcendental number π are read as a sequence. This sequence is random and every possible 2-gram occurs with equal probability. There are ten digits and a hundred possible 2-grams. After a sufficiently large sequence has been examined, the sparsity of the matrix drops and the memory usage to near 100% of the theoretical limit. For an alphabet of size A, the matrix will be sparse with only $A/A^k$ entries for $1-A^{k-1}$ sparsity. FIG. 6 shows a perspective chart 600 derived from the first thirty-eight-hundred digits of π. The frequency scale 610 extends in increments of five from zero to fifteen. No discernible pattern is apparent, indicating random distribution of sequences. This is an example of the best case scenario.

Therefore as a summary of the comparison between conventional and exemplary techniques, the disclosed process is faster by an order of magnitude and employs a comparable usage of memory. Depending on the domain in which the technique is applied, the density of the matrices in the invention may vary, which has an effect on memory efficiency. While in principle one can achieve a 100% memory efficiency, in practice the efficiency is neither 100% nor very low.

Figure 7B:
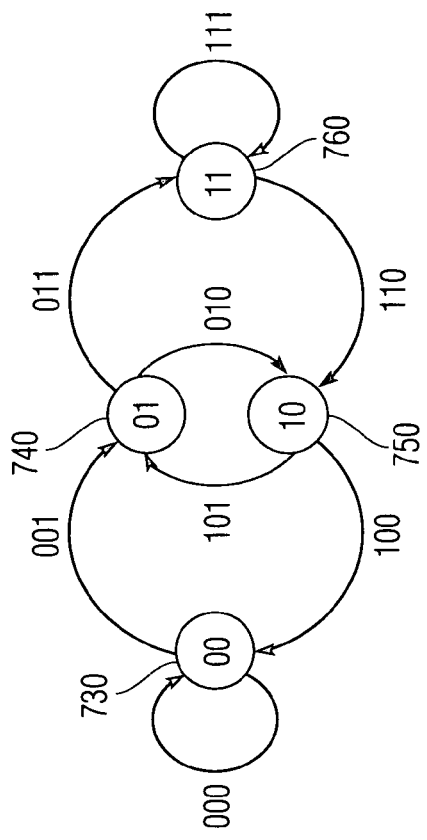
FIGS. 7A and 7B are diagram views of de Bruijn graphs.
Figure 7C:
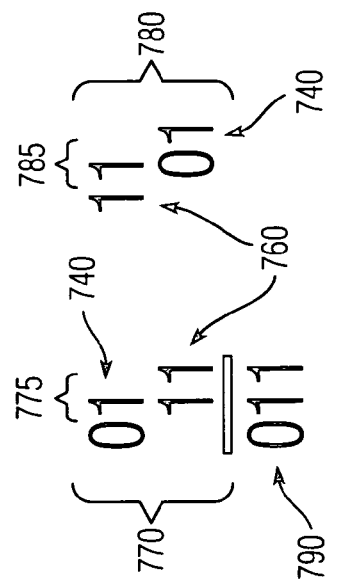
FIG. 7C is a digital view of overlap from the de Bruijn graphs.
Figure 7A:
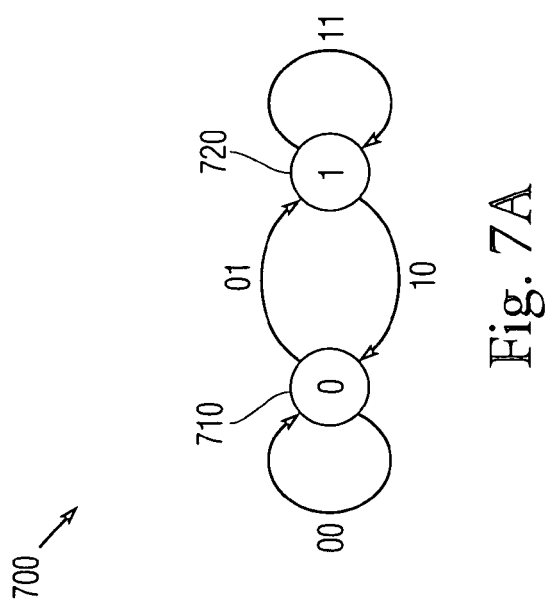

III. Exemplary Structure:

The structure of the algorithm is derived from de Bruijn graphs 700 shown in FIGS. 7A and 7B along with an overlap table in FIG. 7C. This example operates with the domain of binary numbers (i.e., the alphabet of '0 and '1'). FIG. 7A shows the 1-gram graph, based on nodes for zero 710 and one 720, having $2^1$ nodes with $2^2$ valid edges between them denoted by labeled arrows. FIG. 7A shows all the 1-grams as nodes '0' and '1'. At this level, the feasible connections between the 1-grams are represented by connections between the nodes. The valid edges are the only possible combinations of these two symbols. By inverting this graph, each edge can be represented as a node for the 2-gram and additional 3-gram connections can be made. The resulting graph is the 2-gram de Bruijn graph in FIG. 2B with nodes '00' as 730, '01' as 740, '10' as 750 and '11' as 760.

Any 2-gram combination falls on one of those edges. The $2^3$ edges represent all possible 3-grams as any 3-gram combination would fall on one of those edges. The nodes correspond to and are labelled as the set of all possible 2-grams {'00', '01', '10', '11'}. In the next level FIG. 7B, the 2-grams are represented as nodes. Just as in the previous level in FIG. 7A, feasible connections between 2-grams are representative of the next order or 3-grams. Again these connections correspond to and are labelled as the set of all possible 3-grams ('000', '001', '010', '011', '100', '101', '110', '111'). Using these values a set of nodes may be composed into the next level to produce the 3-grams with 4-gram connections and so forth.

Each level n has the following properties. Each valid n-gram is represented by a single node. Each valid (n+1)-gram is represented by a single connection between two n-grams. Each valid connection shows a unidirectional overlap between sequential n-grams. FIG. 7C shows overlays of two 2-gram nodes: from '01' as 740 to '11' as 760 as a first path 770 with a first joint 775, and from '11' as 760 to '01' as 740 as a second path 780 with a second joint 785. As can be seen in FIG. 7O, the first 2-gram node path 770 shows overlap at the first joint 775 (with the end of the first node coinciding with the beginning of the second node), and thus create a valid connection corresponding to '011' node 790. However, the connection is unidirectional so that the second path 780 does not show matching terminal values at the second joint 785 between '11' node 760 and '01' node 740, and therefore cannot create a valid connection in the opposite direction.

Figures 8A, 8B:
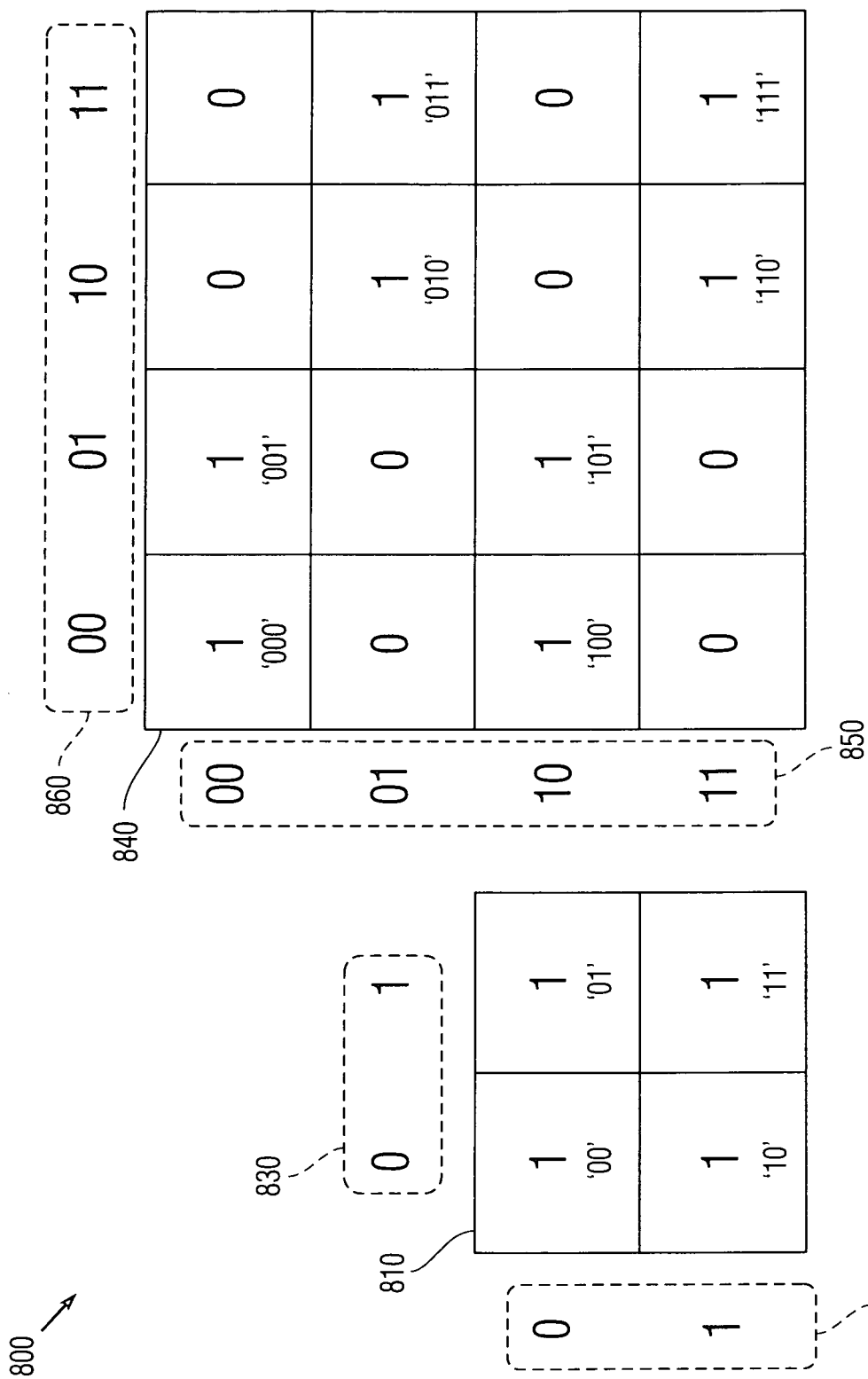
FIGS. 8A and 8B are tabular matrix views of nodes from the de Bruijn graphs.

The mathematical structure that accompanies the exemplary algorithm is based on the de Bruijn graphs 700, but can also be displayed by matrices. FIGS. 8A and 8B are tabular matrix views 800 corresponding to the nodes in the de Bruijn graphs 700 provided in FIGS. 7A and 7B, with each level being represented by a square matrix. FIG. 8A shows a 2×2 matrix 810 with 1-digit rows 820 and columns 830. FIG. 8B shows a 4×4 matrix 840 with 2-digit rows 850 and columns 860. In these tables 810 and 840, the value one in a cell represents a valid connection, while the value zero in a cell represents an invalid connection. The arrows in the graphs 700 correspond to the identified labels in the matrices 800 for the valid connections. Note for example in the 2-gram table 840 that (reading horizontally) the '00' node 730 connects with the '01' node 740 by arrow '001' (identified in the second column and first row), but the '01' node 740 does not connect with the '00' node 730. Because of this, the matrix tables are square (allowing for all connections), but are not symmetric, thereby indicating the directed nature of the tables.

The individual rows and columns of the matrix correspond to the nodes of the graph. The intersection of a row with a column that forms a cell corresponds to the connections of the graph. The value one in the cell indicates that a valid connection exists between the row representing an n-gram and the column representing the next. The value zero in the cell indicates that no valid connection exists. Note that the 2-gram matrix is fairly sparse with only 50% storage efficiency.

Figure 9:
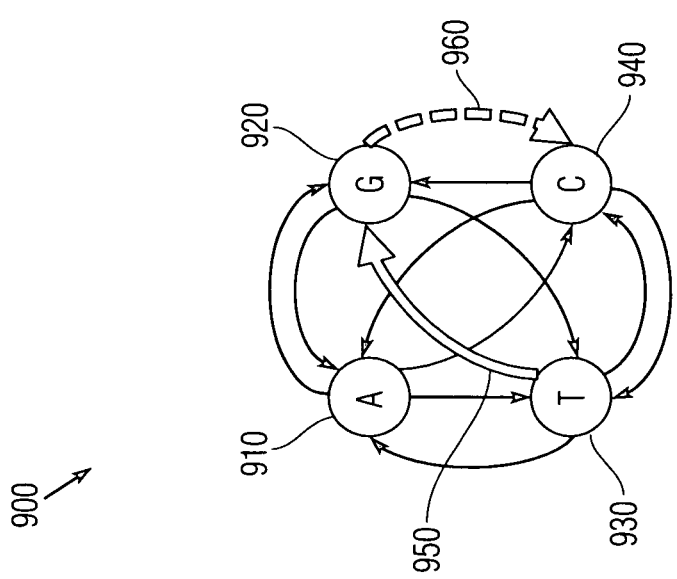
FIG. 9 is a diagram view of a de Bruijn graph for nucleotides.

As another example of the correlation between the de Bruijn graph and the matrix representation described as follows. FIG. 9 shows a graphical view 900 and corresponding matrix for 1-grams based on the genetic nucleotides. These nucleotide nodes are labeled (as in views 500) 'A' for adenine 910, 'G' for guanine 920, 'T' for thymine 930 and 'C' for cytosine 940. Each edge between them indicates a possible connection, shown by arrows. In this example, a solid thick edge 950 represents node 'T' 930 followed by node 'G' 920 to denote sequence 'TG', whereas a broken thick edge 960 represents node 'G' 920 followed by node 'C' 940 to denote sequence 'GC'. Thus the sequence 'TGC' would start at the node 'T' 920 and follow the thick edges 950 and 960 to the node 'C' 940.

Figure 10:
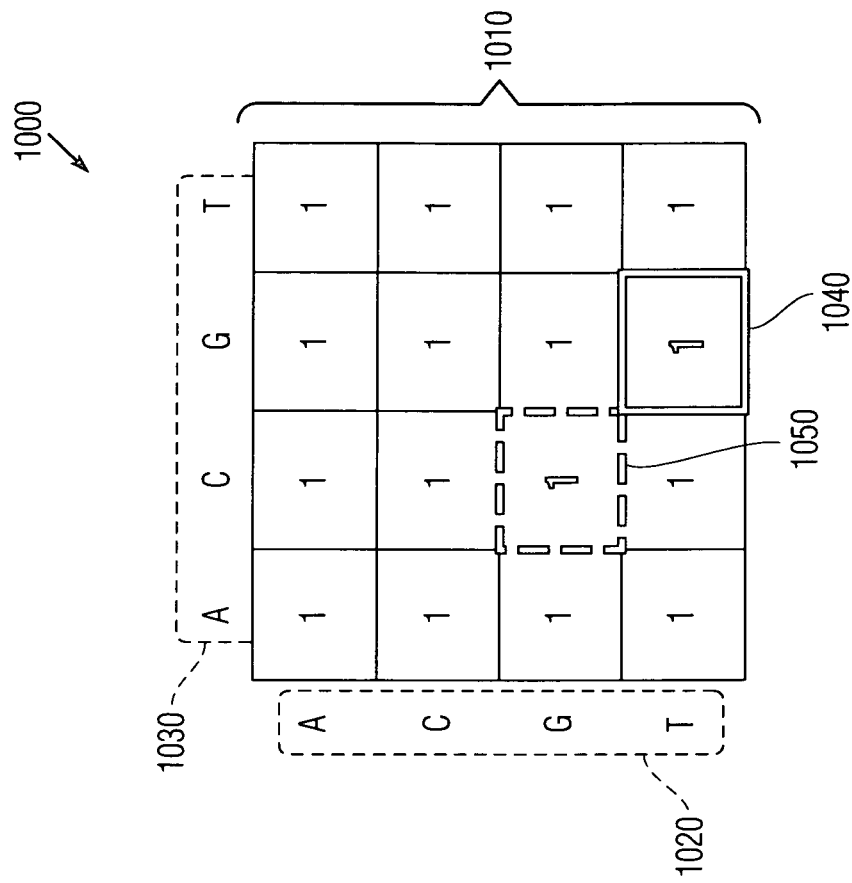
FIG. 10 is a tabular matrix view of the nucleotide nodes.

In a similar manner, any sequence could be expressed as a pathway over the 1-gram de Bruijn graph. FIG. 10 shows a matrix view 1000 of a table 1010 defined by rows 1020 and columns 1030. A solid thick cell 1040 for the intersection of 'TG' corresponds to the solid edge 950. A broken thick cell 1050 for the intersection of 'GC' corresponds to the broken thick edge 960. Note that in this matrix table 1010 there are no zeros, so this is 100% data efficient.

These matrices may be created for each of the levels one through n that are required in the output. Each layer tracks its own frequency counters and corresponds to the level above. As an example the sequence 'TGC' would be processed by first incrementing the block 1040 for 'TG' and then the block 1050 for 'GC'. In each case where the block has been incremented in the 1-gram matrix 1010, corresponding action would be taken in a corresponding 2-gram matrix. This 2-gram matrix, not shown, would include a row for 'TG' and a column for 'GC' and would subsequently be incremented in the intersection corresponding to 'TGC'. This process would proceed to update and increment values at each level upward through the hierarchy.

Figure 11:
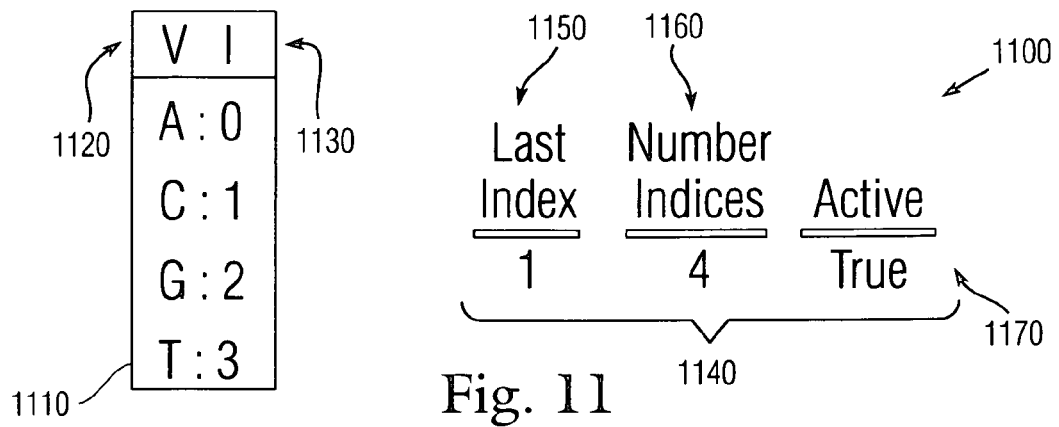
FIG. 11 is a view of parameters for the nucleotide nodes.

In addition to the matrix, there are four additional structures which are necessary for each level in order to perform basic housekeeping tasks. FIG. 11 shows an example structure 1100 corresponding to the matrix 1010 after processing the sequence 'TGC'. This includes a hash table 1110 with the character value key 1120 and its corresponding value index 1130. The hash table 1110 is used to track the values corresponding to the matrix indices. In addition, a list of parameters 1140 aids in accounting for progress and status. A last index 1150 (i.e., most recent index encountered in the sequence), a number of key indices 1160 (in the hash table) and a logical active state 1170 of that level.

The variable last index 1150 tracks the most recent preceding value that was processed. As indicated by the hash table 1110, the last value 'C' corresponds to the index one. Thus, the index one appears for the last index 1150. The number of indices 1160 held in the hash table 1110 is identified as four. That number also corresponds to the next matrix index, making it a trivial process to add an additional index when required or to decide on resizing the matrix. The logic variable 1170 indicates whether the table 1110 is currently active. An inactive table (i.e., 'false') has not yet processed any values and must be activated when this occurs. Once activated (i.e., 'true'), any additional processed values will require a corresponding action in the next highest table.

Figure 12:
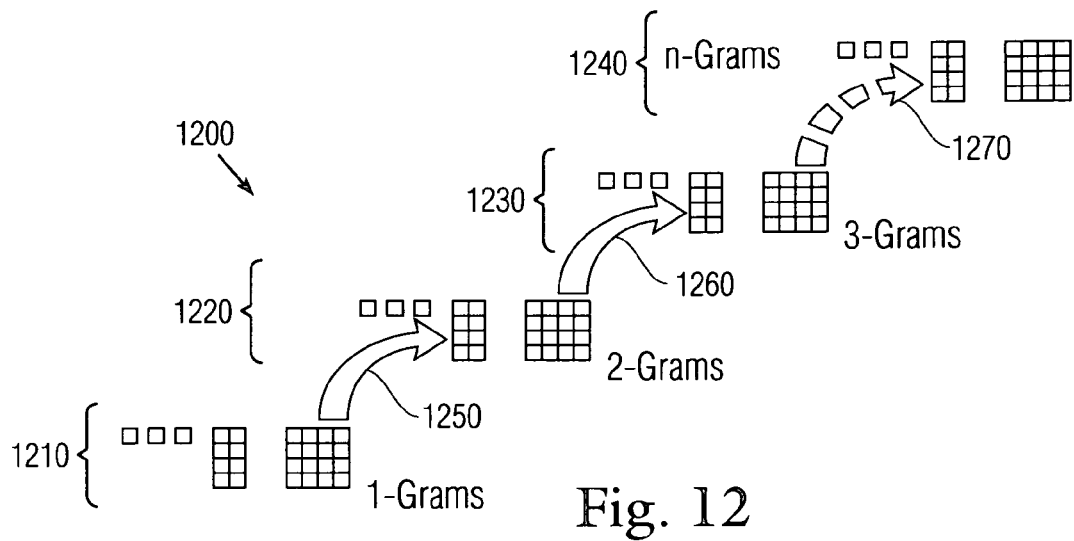
FIG. 12 is a diagram view of relationships between generic n-gram layers.

In summary the accompanying structure is a homogenous hierarchy which relates cell values at the $n^{th}$ layer with index values at the $n+1^{st}$ layer. As shown in FIG. 12, each layer has its own matrix 1010, hash table 1110, last index 1150, number variable 1160 and active variable 1170. In order to simultaneously process all subsequences of size n or smaller the first layer tracks 1-grams, the second 2-grams, the third 3-grams and so on until the final $n^{th}$ layer tracks n-grams.

Figure 13:
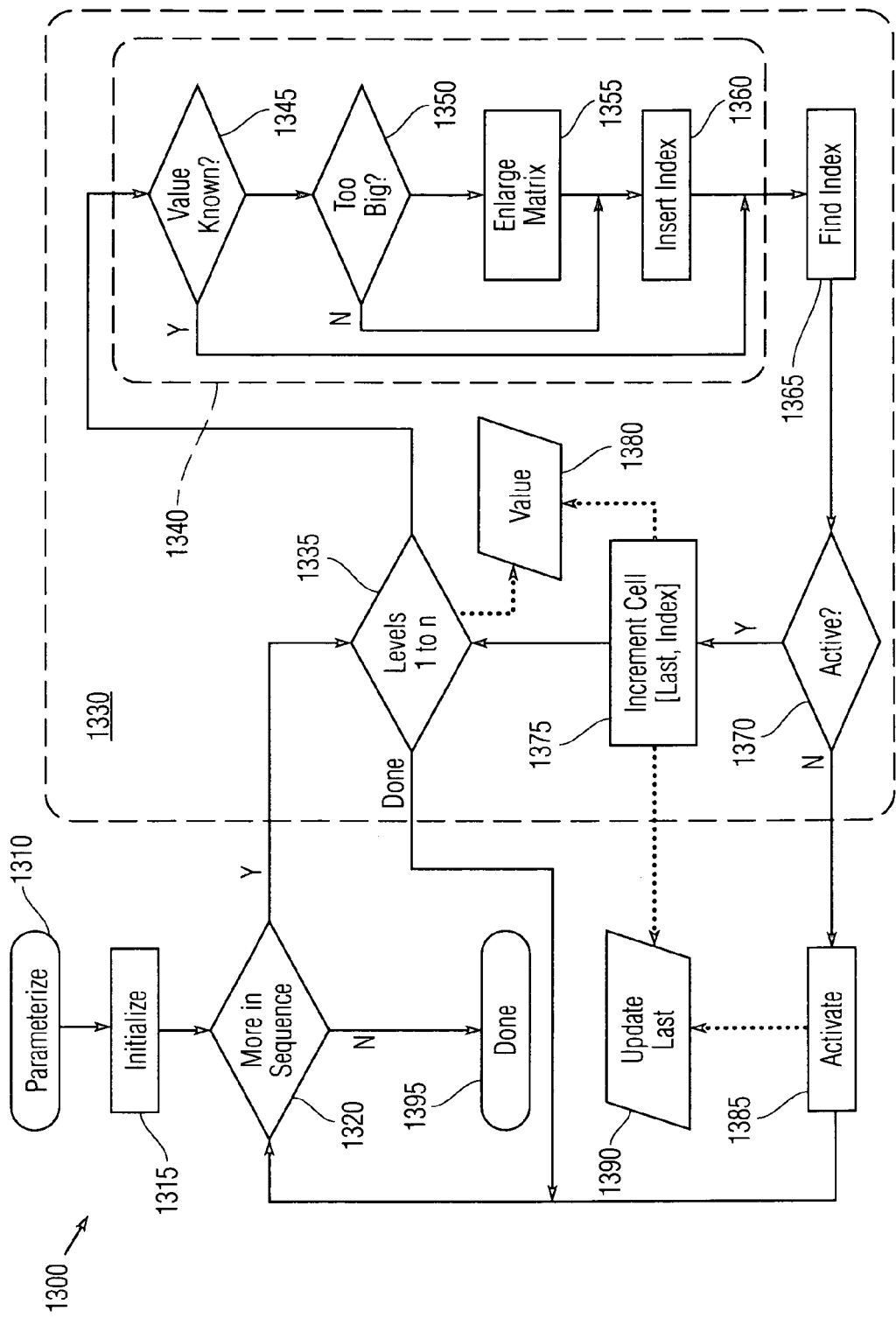
FIG. 13 is a flowchart diagram view of procedural instructions.

IV. Algorithm Description:

The algorithm portion in exemplary embodiments is shown in FIG. 13 as a flowchart 1300. The process begins with parameterization 1310 of an input sequence (i.e., digitally decomposing and ordering the characters or other symbolic representation in the sequence for input) followed by an instantiation phase 1315 (i.e., establishing the hash tables and matrices and setting select parameters to default values). A first query 1320 determines whether additional characters in the sequence remain. If affirmative, the process continues to a first iteration loop 1330 in which a second query 1335 determines the last index L 1150 from one to n and begins to process the current value (at operation 1380). The process continues to a second iteration loop 1340 in which a third query 1345 determines whether the value of the input character is known (i.e., the character having been previously encountered and recognized). If negative, a fourth query 1350 determines whether the value exceeds the previously established hash table and matrix size.

If affirmative, an expansion operation 1355 expands the matrix to include additional rows and columns and continues to operation 1360. Otherwise, the process skips operation 1355 and continues to operation 1360 to be unified with the alternative operational flow. The process continues to an insert index operation 1360. Upon completion or if the third query 1345 is affirmative the process exits the second loop 1340 and continues to a find index operation 1365. A fifth query 1370 determines whether the current level is active. If affirmative, the process continues to a cell increment operation 1375 and returns to the second query 1335.

The increment operation 1375 calculates the new index value 1380, which will be processed in the next level and assigns new last index value 1390. Upon returning to the second query 1335, the level is incremented and the new value 1380 is processed. When the $n^{th}$ level has been processed, the second query 1335 exits the first loop 1330 and returns to the first query 1320. If the fourth query 1370 is negative, the process exits the first loop 1330 and proceeds to an activation operation 1385 to activate the index. The operation 1385 updates the last index value 1390. The activate operation 1385 returns to the first query 1320. Additionally, when the second query 1335 completes the levels, the process returns to the first query 1320. When no further additional characters remain in sequence in the first query 1320, the operation is completed and terminates 1395.

Additionally, the algorithm portion in exemplary embodiments is shown in FIG. 14 as instruction pseudocode 1400. This instruction set can be broken into sub sections including parameterization 1410 (lines 1-2), initialization 1420 (lines 5-9), structure resizing 1430 (lines 19-30) and processing 1440 (lines 35-46). Much of the code also falls into loops. There is an overarching loop 1450 (lines 12-48) that repeats for each new value in the sequence. An inner loop 1460 (lines 17-47) repeats operations for each level of the structure.

The algorithm may be parameterized to enable any maximum n-gram length, but in this example code, the length is set as ten. This value affects the size of the structure and moderately alters the speed of execution. Obviously processing up to 5-grams will be faster than 500-grams. As noted before, examples provided herein demonstrate the exemplary process for explanatory purposes, rather than provide a practical example for solution. However, in order for this to significantly alter performance, the size of n must greatly exceed the size of the sequence itself. Similarly, the starting $k_1$ dimension of the hash table is a parameterized value, but in this example code $k_1$ is set as fifteen. This value also affects the efficiency of structure resizing as each resize is a geometric progression (i.e., $k_1 \cdot 2^0$, $k_1 \cdot 2^1$, $k_1 \cdot 2^2$, etc., yielding $k_1$, $2k_1$, $4k_1$, ...). While selecting an appropriate value for this size $k_1$ can be tailored to the specific task, this only amounts to a multiplier on the basic progression of powers of two and thus has no permanent effect on performance.

The initialization phase 1315 creates the matrix, hash table 1110, number 1160, last 1150 and active 1170 variables for each level. This process is fairly straight forward. One can expect that the default value for each matrix cell is zero. By the same token, the number N of indices 1160 must be initialized to a default value of zero. The last index L 1150 has no such requirement, as any prior value will be replaced and thus can be discarded. Active A 1170 is also required to initialize to the default value of 'false'. The hash table 1110 has no initial content requirements. These values are required as part of initialization.

Figure 15:
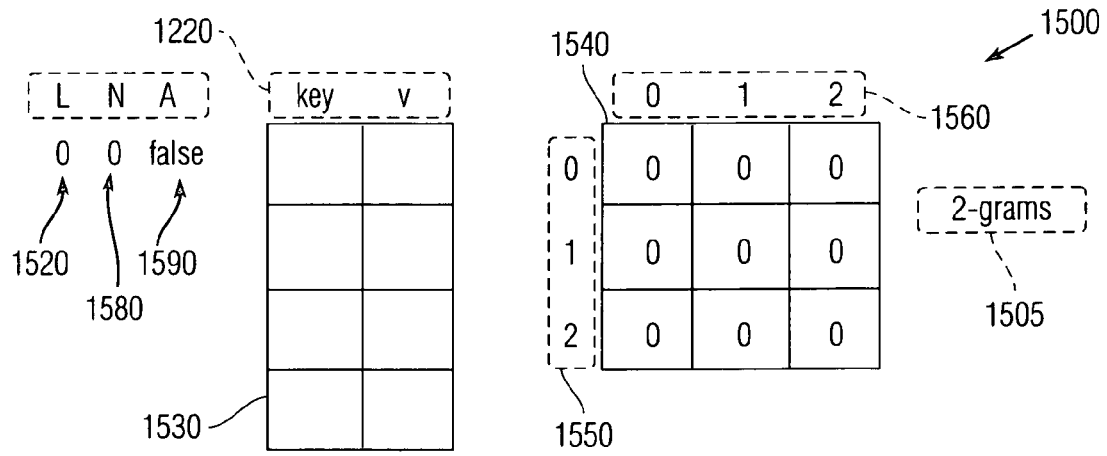
FIG. 15 is a tabular matrix view of a generic explanatory matrix and parameters.

FIG. 15 shows a tabular schematic view 1500 of analysis process format for some n-gram identified value 1505. Parameters 1510 corresponding to the list 1140 include last L, number N and active A. Identification columns 1520 for a hash table 1530 (analogous to the hash table 1110) includes the subsequence key 1120 (e.g., character) and its corresponding index value v 1130. A square matrix 1540 is defined by rows 1550 and columns 1560, with labels determined by the keys 1120. The sequence for characters are presented in order of row and column for first and second indices in the matrix, although artisans of ordinary skill will recognize that this arrangement represents an exemplary convention and can be interchanged without departing from the scope of the invention. Beginning establishment of parameters 1510 includes setting last 1570 as L=0, and initializing number 1580 as N=0 and active 1590 as A='false'. Subsequently, the index value v 1130 in the hash table 1530 will be one less than the number N 1580 as representative counters.

The two loops process each value from the sequence. The overarching loop 1330 reads in a single value (i.e., a 1-gram) from some form of data stream. The specific implementation is unimportant and may be chosen at the convenience of the system. That value, stored temporarily on line 14, becomes the loop invariant for the inner loop 1340. Upon the start of each iteration of the inner loop 1340, the variable value shall contain the n-gram that will be represented in the column of the matrix at that level. The value is changed on line 44 of the pseudocode 1400 as part of the process corresponding to the increment operation 1375. The joining operation operates to join or overlap the last and current values. Thus for the first iteration, the value might be character 'a', but in each subsequent iteration the value aggregates some portion based on the last values processed (i.e., 'ab', 'abc', 'abcd', etc.).

The structure resizing is triggered based on the number of indices used. This can only occur when a new key is discovered, and so this is the first check on line 19 of the pseudocode 1400. After that point, the key must be added to the hash table 1110 and a new index added on line 30. In comparison with the size of the matrix, the number of indices should always be smaller (i.e., a $5^{th}$ index will be out of bounds on a 4×4 matrix). Thus if that bound is exceeded at line 21, the matrix must be resized. Lines 24-27 in structure resizing 1430 merely exhibit the calculation of current matrix size, creation of a larger matrix, copying the contents of the smaller matrix and storing the copy. Notes that the copying process is assumed and not shown in this pseudocode 1400.

Whether an index is either new or otherwise, the index is extracted from the hash table 1110 on line 33 and operation begins. Processing differs depending on the logic state of the active variable 1170. An inactive hash table ('false') has no last value 1150 and thus has no ability to calculate the operation on line 43. For this situation, there is also no last value to aggregate on line 44. These actions are required of all active hash tables in order to pass the aggregate value up to the next level. The inactive layer must first become active ('true'). The break statement on line 39 indicates that the inner loop 1440 will terminate early if an inactive table is found. Thus, if any hash table 1110 has no aggregate value to pass on, then there is naturally no need to proceed to the next level. Note that both active and inactive tables must update the last index value 1150, as shown in operations 1385 and 1375.

V. Process Example:

In order to demonstrate the algorithm in operation an example has been prepared. This example processes a sequence S of letters corresponding to the word 'mississippi' (denoting the geographic place-name). The structure is set up to process up to 3-grams and several relevant iterations are shown. These iterations were selected only to demonstrate the operation of the algorithm and are not exhaustive. As the algorithm progresses each level becomes active and then begins to store frequency data. Using the sequence S as defined, the following states describe the first six iterations of the algorithm as an exemplary process.

Figure 16A:
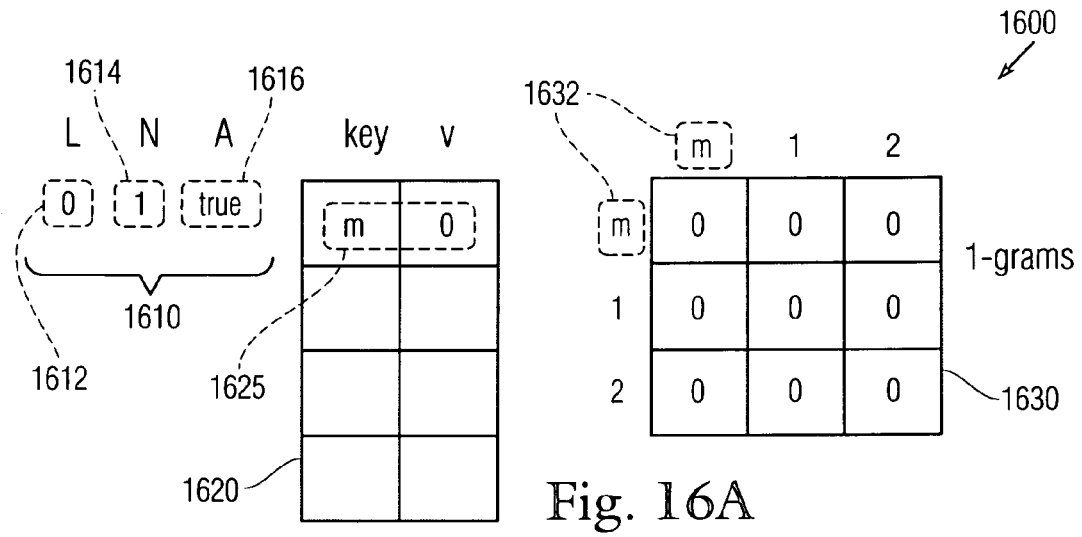
FIGS. 16A, 16B and 16C are tabular matrix views for a first iteration.
Figure 16B:
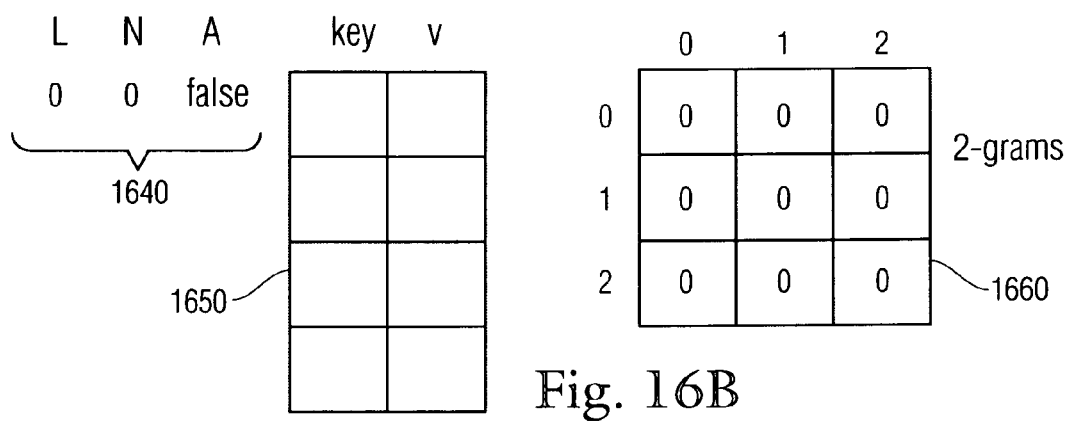
Figure 16C:
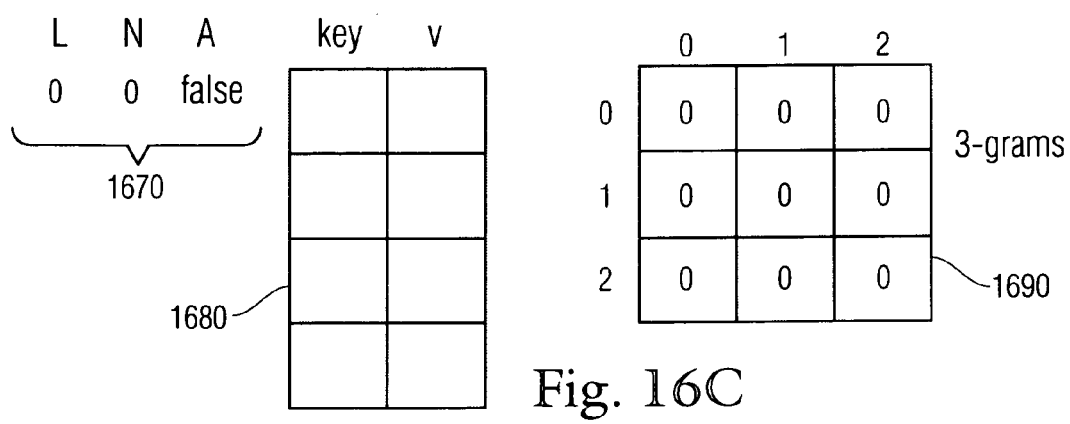

Iteration 1—Processing 'm': In this initial iteration, the full operation of all levels is not visible. Even the changes performed on the variables may not be readily apparent. FIGS. 16A, 16B and 16C show tabular schematics 1600 of 1-gram, 2-gram and 3-gram graphs for the first iteration. FIG. 16A shows 1-gram parameter values 1610 with the last index set to zero 1612 corresponding to the index of the first key 'm', number N 1614 incrementing to one, and switching active A to 'true' 1616. FIG. 16A further shows a hash table 1620 with filled row 1625 denoting 1-gram 'm' and index zero, and a matrix 1630 with 'm'. Introduction of the 1-gram 'm' activates the matrix 1630, albeit with no non-zero cell. For convenience, the matrix 1630 shows 'm' 1632 as corresponding to the first row 1625 in the hash table 1620. The matrix 1630 shows 'm' 1632 substituting for zero in the first row (in 1550) and column (in 1560).

The letter 'm' is not found in the first (1-gram) level hash table 1620, which in fact has been empty. Thus this character is added to the key and an index of zero is assigned in the row 1625 and the number of indices 1614 is advanced (i.e., incremented) from zero to one. The 1-gram level is activated, thus switching the active state 1616 to 'true'. Although not visually obvious, the current index of zero corresponding to the index for the 'm' character is stored under L for the last index 1612. FIG. 16B shows 2-gram parameter values 1640, hash table 1650 and matrix 1660. No change has occurred from initial default settings and the hash table 1650 remains empty. FIG. 16C shows 3-gram parameter values 1670, hash table 1680 and matrix 1690. No change has occurred.

Iteration 2—Processing 'i': FIGS. 17A, 17B and 17C show tabular schematics 1700 of 1-gram, 2-gram and 3-gram graphs after completing the second iteration. FIG. 17A shows 1-gram parameter values 1710 with the last index 1712 set to one corresponding to the index of the second key 'i', the index number N 1714 incrementing to two, a hash table 1720 with filled row 1725 denoting 1-gram 'i' and index one, and a matrix 1730 with 'i' 1732. The letter 'i' is not found in the first (1-gram) level hash table 1720, and thus this character is added to the key and an index of one is assigned in the row 1725 such that the number of indices 1714 increments from one to two. For convenience, the matrix 1730 shows 'i' 1732 as corresponding to the second row 1725 in the hash table 1720. The matrix 1730 shows 'i' 1732 substituting for one in the first row (in 1550) and column (in 1560). Moreover, an occurrence of 'm' followed by 'i' is indicated by value one in the cell 1734 at the first row and second column.

The introduction of a second letter continues the process by activating a second 2-gram level. FIG. 17B shows 2-gram parameter values 1740 with the last index 1742 set to zero, an increment of number N 1744 to one, and switch in active A to 'true' 1746 for the 2-gram level. FIG. 17B further shows a hash table 1750 with filled row 1755 denoting 2-gram 'mi' and index zero (to which the last index 1742 is set), and a matrix 1760 with 'mi' 1762 substituting for zero in the first row (in 1550) and first column (in 1560). FIG. 17C shows 3-gram parameter values 1770, hash table 1780 and matrix 1790. No change has occurred.

For the second iteration, the changes become more apparent. The 1-gram parameter values 1710 indicate that the level is active, with two indices at 1714, and that the last index 1712 was set to one. The hash table 1720 has records of two 1-grams along with their corresponding index values. For convenience the matrix 1730 shows '1' 1732 where the corresponding index was found in the second row and second column. Also in matrix 1730, the increment in the cell 1734 with value one corresponds to a single occurrence of the 2-gram 'mi' and resulting activation at 1746 of the 2-gram level.

The 2-gram parameter values 1740 indicate that the level is active at 1746, with a single index 1744, and that the last index 1742 was zero. The hash table 1750 has a record of the 2-gram 'mi' at row 1755 and the corresponding index zero. For convenience the matrix 1760 shows the 2-gram 'mi' 1762 where the corresponding index was added in the first row and first column. The sequence 'mi' is not found in the second level hash table 1750 so this string is added to the key, the index of zero is assigned in row 1755, and the 2-gram number of indices 1744 is incremented.

Iteration 3—Processing 's': FIGS. 18A, 18B and 18C show tabular schematics 1800 of 1-gram, 2-gram and 3-gram graphs after the third iteration. This is the first iteration that produces changes on each level. FIG. 18A shows 1-gram parameter values 1810 with the last index 1812 being set to two corresponding to the index of the 1-gram 's', an increment of number N 1814 to three, a hash table 1820 with filled row 1825 denoting 1-gram 's' and index two, and a matrix 1830 with 's' 1832 substituting one in the third row and third column. For convenience, the matrix 1830 shows 's' 1832 as corresponding to the third row 1825 in the hash table 1820. Moreover, an occurrence of 'i' followed by 's' is indicated by value one in the cell 1834 at the second row and third column. The hash table 1820 has records of three 1-grams along with their corresponding index values.

FIG. 18B shows 2-gram parameter values 1840 with the last index 1842 incremented to one, an increment of number N 1844 to two, a hash table 1850 with filled row 1855 denoting 2-gram 'is' and index one and a matrix 1860 with 'is' 1862 substituting one in the second row and second column. For convenience, the matrix 1860 shows 'is' 1862 as corresponding to the second row 1855 in the hash table 1850. Moreover, an occurrence of 'mi' followed by 'is' is indicated by value one in the cell 1864 at the first row and second column.

FIG. 18C shows 3-gram parameter values 1870 with the last index 1872 set to zero, an increment of number N 1874 to one and switch in active A to 'true' 1876. FIG. 18C further shows a hash table 1880 with filled row 1885 denoting 3-gram 'mis' and index zero, and a matrix 1890 with 'mis' 1892 substituting zero in the first row and first column. The matrix 1890 shows 'mis' 1892 as corresponding to the first row 1855 in the hash table 1850.

The letter 's' is not found in the level one hash 1820, so this letter is added to the key, the index of two is assigned in row 1825, and the number of indices is incremented from two to three. The level is active, so the cell 1834 in matrix 1830 is incremented. The current index is stored as L 1812. Note that the newly incremented value of N 1844 corresponds to the 2-gram 'is' (minus one), and this aggregate value is processed at the next level.

The 2-gram 'is' is not found in the level two hash 1850 so the 2-gram is added to the key, the index of one is assigned in row 1855, and the number of indices is incremented. The hash table 1850 has a record of two 2-grams along with their corresponding index values. The 3-gram parameter values 1870 indicate that the level is active, with one index and that the last index was zero. The hash table 1880 has a record of the 3-gram 'mis' and its corresponding index zero.

Figures 19A, 19B, 19C:
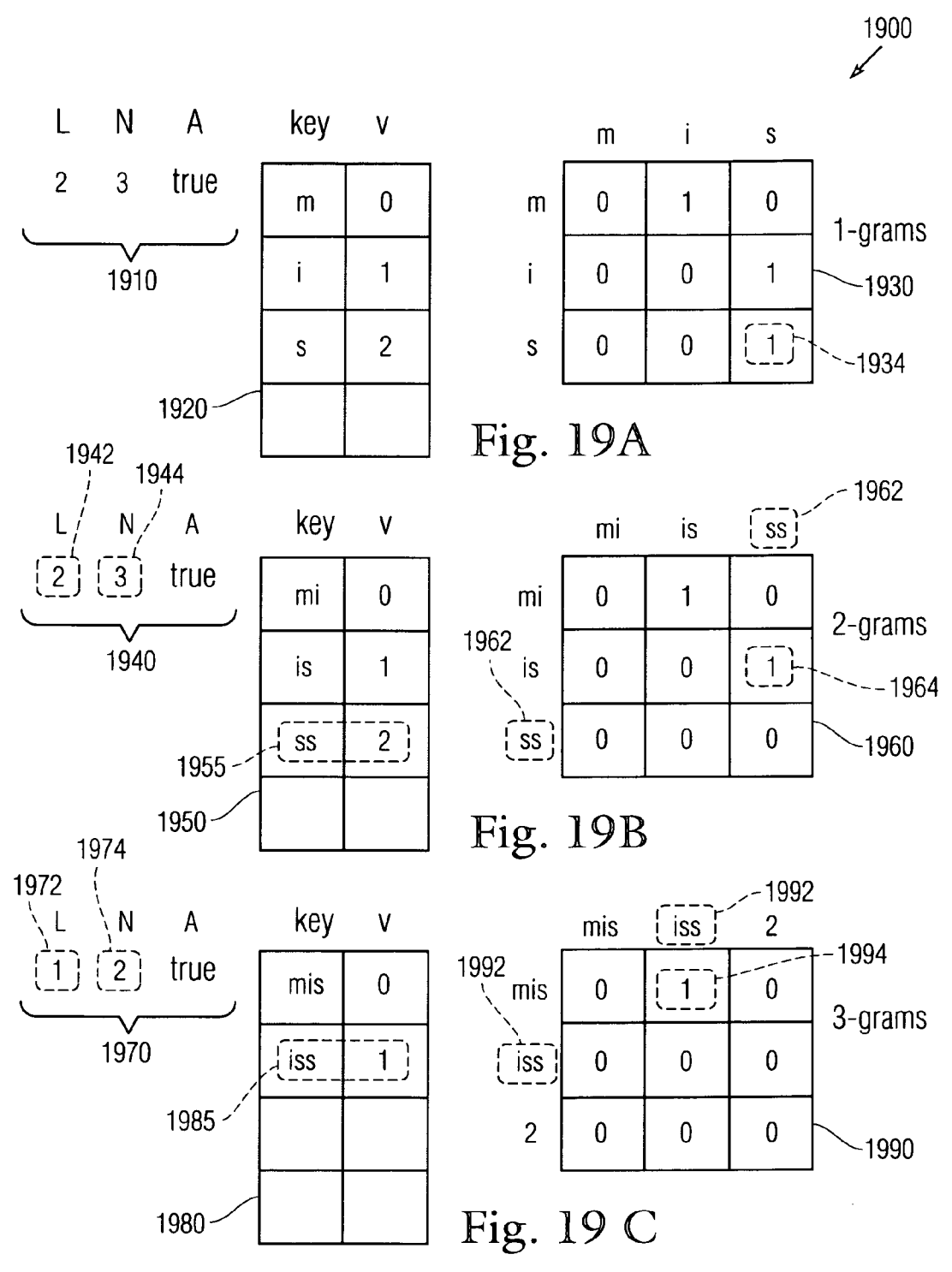

Iteration 4—Processing 's': FIGS. 19A, 19B and 19C show tabular schematics 1900 of 1-gram, 2-gram and 3-gram graphs after the fourth iteration. FIG. 19A shows 1-gram parameter values 1910 with no apparent changes, a hash table 1920 with no changes, and a matrix 1930. A repeated occurrence of 's' is indicated by value one in the cell 1934 at the third row and third column. FIG. 19B shows 2-gram parameter values 1940 with the last index 1942 incremented to two, an increment of number N 1944 to three, a hash table 1950 with filled row 1955 denoting 2-gram 'ss' and index two, and a matrix 1860 with 'ss' 1962 substituting two in the third row and third column. The matrix 1960 shows 'ss' 1962 as corresponding to the third row 1955 in the hash table 1950.

Moreover, an occurrence of 'is' followed by 'ss' is indicated by value one in the cell 1964 at the second row and third column. FIG. 19C shows 3-gram parameter values 1970 with the last index 1972 set to one, an increment of number N 1974 to two a hash table 1980 with filled row 1985 denoting 3-gram 'iss' and index one, and a matrix 1990 with 'iss' 1992 substituting one in the second row and second column. The matrix 1990 shows 'iss' 1992 as corresponding to the second row 1985 in the hash table 1980. Also in matrix 1990, an occurrence of 'mis' followed by 'iss' corresponds to one occurrence of the 4-gram 'miss' with the 2-gram end of the former coinciding with the 2-gram beginning of the latter as indicated by the value one in the cell 1994 at the first row and second column.

In this fourth iteration, the tedium of reciting each step can be omitted. The 1-gram 's' is processed at the first level, the 2-gram 'ss' at the second level and the 3-gram 'iss' at the third level. Note that 1-gram para meters 1910 indicate that there are only three indices because 's' already appears in the hash table. When that value was found, no new record was added and the value N was not incremented. This corresponds to the pseudo-code 1400 where a positive answer on line 19 causes resizing 1430 to be skipped. The effect on 19B and 19C is similar to those shown in previous iterations.

Figure 20B:
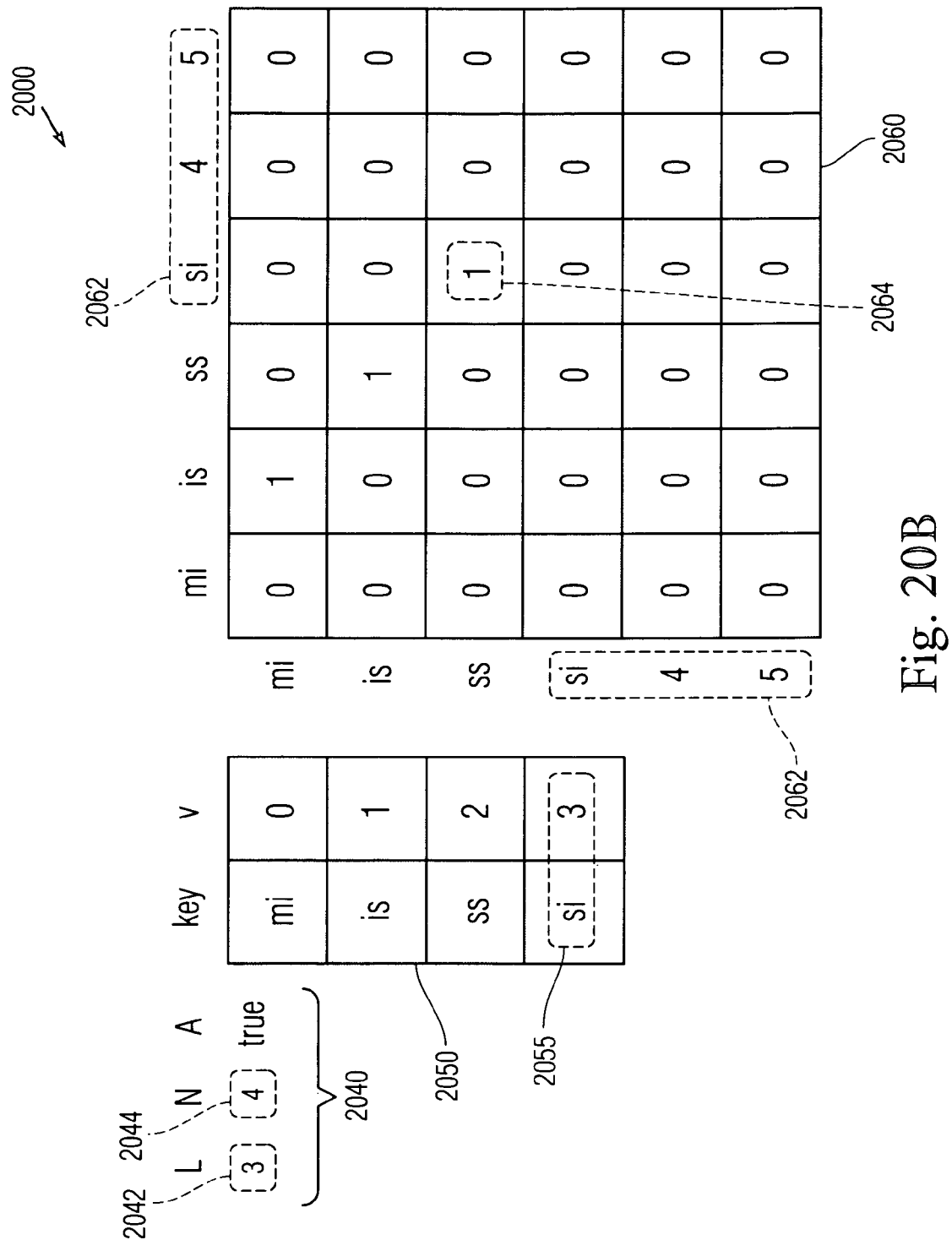

Iteration 5—Processing 'i': FIGS. 20A, 20B and 20C show tabular schematics 2000 of 1-gram, 2-gram and 3-gram graphs after the fifth iteration. FIG. 20A shows 1-gram parameter values 2010 with the last index 2012 reset to one that corresponds to the index value of letter 'i' having repeated in the sequence S, a hash table 2020 with no change (as no new letter has been added), and a matrix 2030. An occurrence of 's' followed by 'i' is indicated by value one in the cell 2034 at the third row and second column. FIG. 20B shows 2-gram parameter values 2040 with the last index 2042 set to three corresponding to the 2-gram 'si', an increment of number N 2044 from three to four, an expanded hash table 2050 with added row 2055 denoting 2-gram 'si' and index three, and an expanded matrix 2060 with entries 'si 4 5' 2062 adding third, fourth and fifth rows and columns. The matrix 2060 shows part of 'si 4 5' 2062 as corresponding to the fourth row 2055 in the hash table 2050.

Moreover, an occurrence of 'ss' followed by 'si' is indicated by value one in the cell 2064 at the third row and fourth column. FIG. 20C shows 3-gram parameter values 2070 with the last index 2072 incremented to two, an increment of number N 2074 to three, a hash table 2080 with filled row 2085 denoting 3-gram 'ssi' and index two and a matrix 2090 with 'ssi' 2092 substituting two in the third row and third column. The matrix 2090 shows 'ssi' 2092 as corresponding to the third row 2085 in the hash table 2080. Also in matrix 2090, an occurrence of 'iss' followed by 'ssi' corresponds to one occurrence of the 4-gram 'issi' as indicated by the value one in the cell 2094 at the second row and third column.

Again, the description of this fifth iteration focuses only on events of note. The 1-gram 'i' is processed at the first level, the 2-gram 'si' at the second level and the 3-gram 'ssi' at the third level. Note that the first level already has this 1-gram, so no change occurs in the hash table 2020 nor in the N parameter in values 2010. However, the 1-gram L parameter of last index 2012 sets to one, corresponding to the 1-gram 'i'. Note also that because 'si' is the fourth 2-gram, the hash table 2050 expands in size. The doubling in the dimension of the index creates a quadruple effect on the totals size of the matrix 2060. Corresponding changes in the hash table 2050 and N parameter number 2044 indicate that there are now four indices instead of the previous three. The remaining changes to FIGS. 20B and 20C are consistent with those shown in previous iterations.

The 1-gram parameter values 2010 indicate that the level is active, with three indices, and that the last index was set to one. The hash table 2020 has records of three 1-grams along with their corresponding index values. Also in matrix 2030, the increment corresponds to an occurrence of the 2-gram 'si'. The 2-gram parameter values 2040 indicate that the level is active with four indices, and that the last index was three. The hash table 2050 has records of four 2-grams along with their corresponding index values. The matrix 2060 shows 'si' 2062 where the corresponding index was found in the fourth column and fourth row. Also in matrix 2060, the increment in number 2044 corresponds to one (i.e., first) occurrence of the 3-gram 'ssi'.

The 3-gram parameter values 2070 indicate that the level is active, with three indices and that the last index 2072 was two, corresponding to 3-gram 'ssi'. The hash table 2080 has records of three 3-grams along with their corresponding index values. For convenience, the matrix 2090 shows 'ssi' 2092 where the corresponding index was found in the third column and third row. Also in matrix 2090, the increment for number 2074 corresponds to an occurrence of the 4-gram 'issi' as denoted at cell 2094.

Figure 21B:
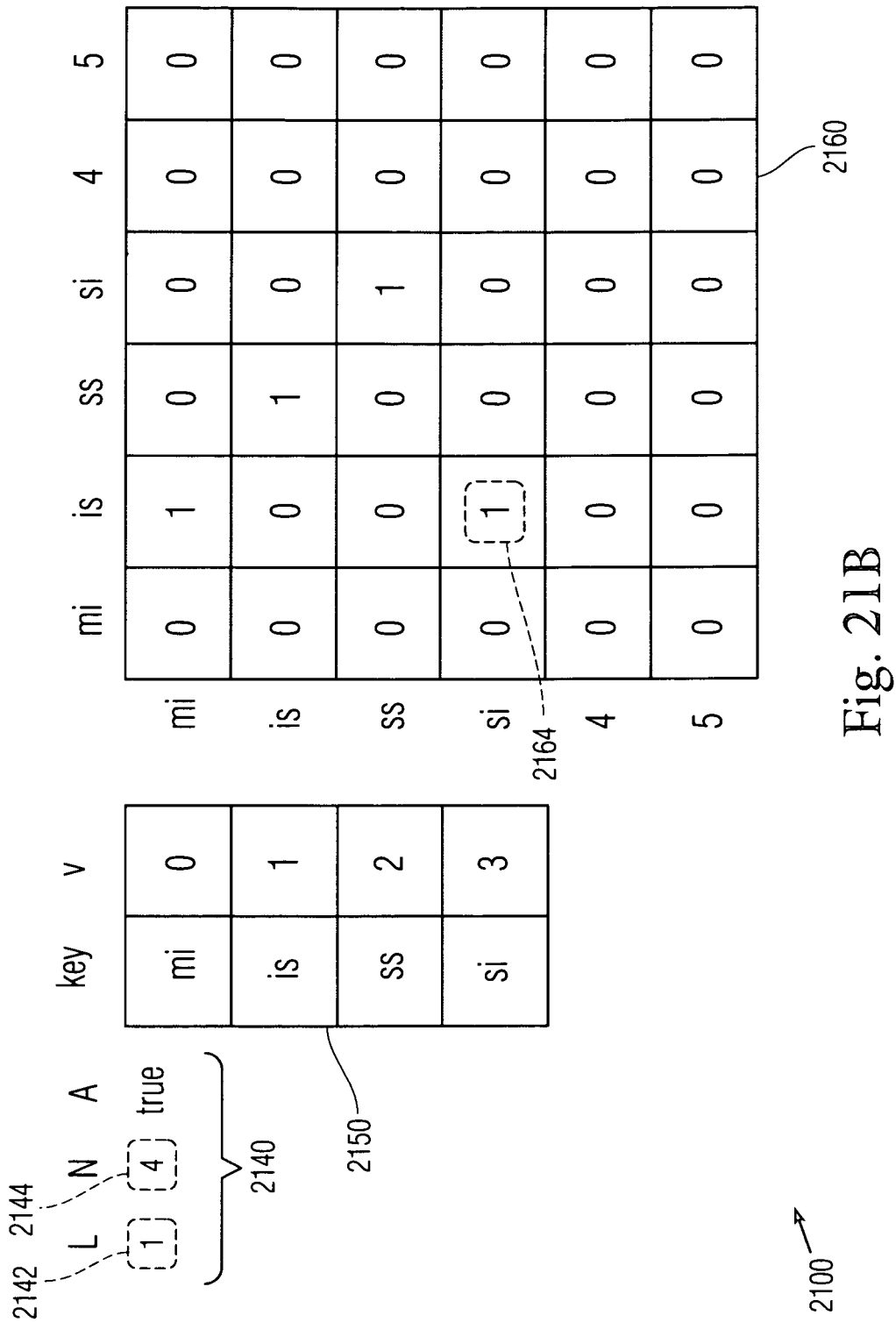
Figure 21C:
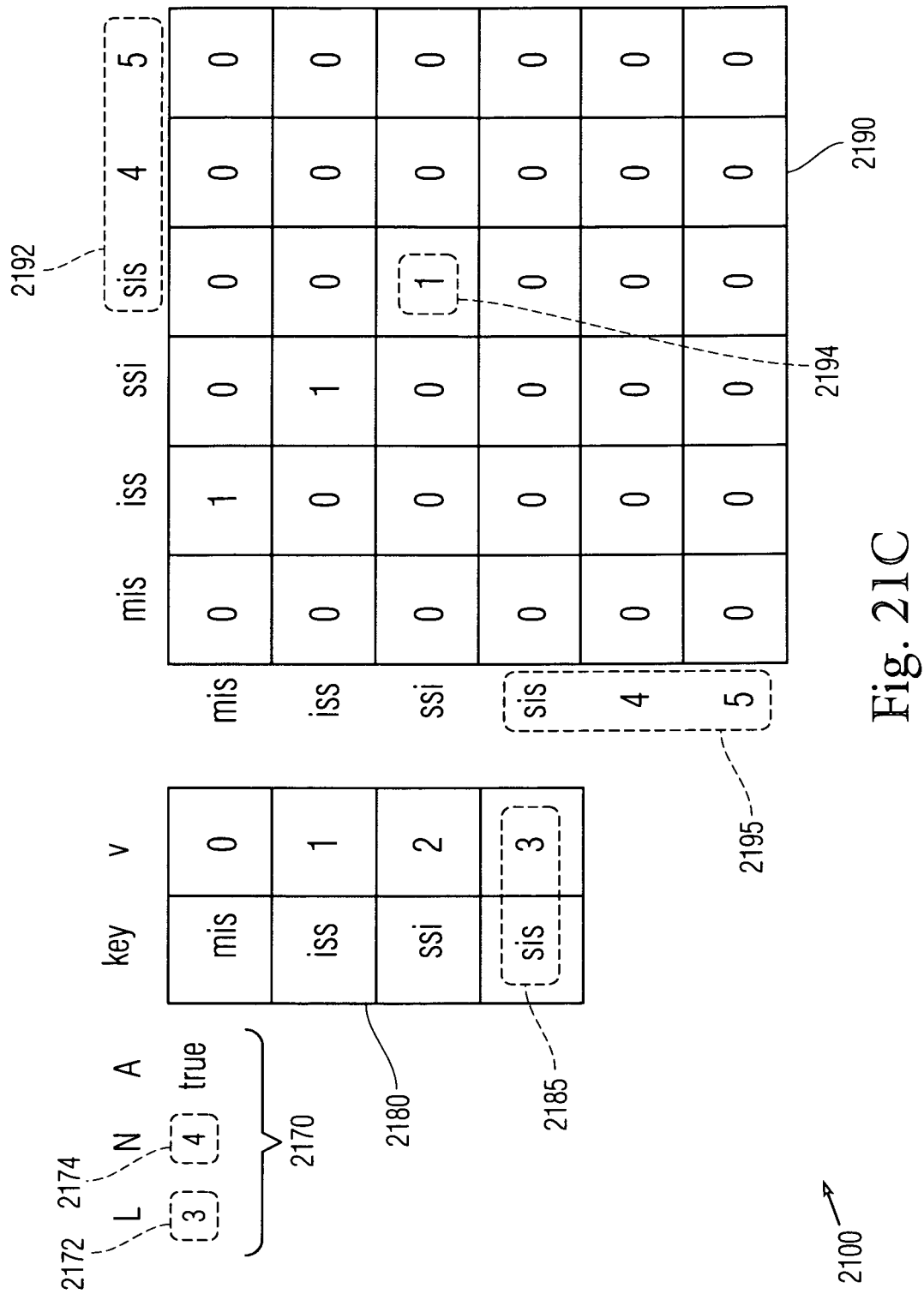

Iteration 6—Processing 's': This is the last iteration that is shown in detail. FIGS. 21A, 21B and 21C show tabular schematics 2100 of 1-gram, 2-gram and 3-gram graphs after the sixth iteration. FIG. 21A shows 1-gram parameter values 2110 with the last index 2112 set to two, a hash table 2120 with no change, and a matrix 2130. Another occurrence of 's' followed by 'i' is indicated by value two in the cell 2136 at the second row and third column, incrementing the value from prior cell 1834 in that array position. FIG. 21B shows 2-gram parameter values 2140 with the last index 2142 reset to one (corresponding to repeated 2-gram 'is'), an increment of number N 2144 to four, a hash table 2150 with no change, and a matrix 2160. An occurrence of 'si' followed by 'is' is indicated by value one in the cell 2164 at the fourth row and second column.

FIG. 21C shows 3-gram parameter values 2170 with the last index 2172 set to three, an increment of number N 2174 to four, a hash table 2180 with added row 2185 denoting 3-gram 'sis' and index three, and an expanded matrix 2190 with 'sis 4 5' 2192 expanding into the fourth through sixth rows and columns. The matrix 2190 shows 'sis 4 5' 2192 as corresponding to the fourth row 2185 in the hash table 2180 and additional unassigned rows and columns. Also in matrix 2190, an occurrence of 'ssi' followed by 'sis' corresponds to an occurrence of the 4-gram 'ssis' as indicated by the value one in the cell 2194 at the third row and fourth column.

The 1-gram 's' is processed at the first level, the 2-gram 'is' at the second level and the 3-gram 'sis' at the third level. Note that for both the first and second level these n-grams have already been seen, so there is no change in the hash tables or N parameters. However, the 1-gram L parameter last index 2112 and 2-gram L last index parameter 2142 have been changed to indicate the last indices of two and one corresponding to 's' and 'is' respectively. Note also that in 1-gram matrix 2130 increment of number 2114 is the first repeated occurrence of a 2-gram, and thus a value greater than one in any matrix. Finally, the increase of matrix 2190 is necessitated by the accommodation of a fourth index value. Again, this doubling effect in the indices increases the matrix size by a factor of four. All other changes are consistent with what has been shown in previous iterations.

The 1-gram parameter values 2110 indicate that the level is active, with three indices and that the last index 2112 was two, corresponding to the 1-gram 's' in a repeat encounter. The hash table 2120 has records of three 1-grams along with their corresponding index values. Also in matrix 2130, the increment number 2114 corresponds to two occurrences of the 2-gram 'is'. The 2-gram parameter values 2140 indicate that the level is active, with four indices, and that the last index 2142 is set to one corresponding to the sequence 'is' again. The hash table 2150 has records of four 2-grams along with their corresponding index values. Also in matrix 2160, the increment number 2144 corresponds to one occurrence of the 3-gram 'sis' denoted at cell 2164.

The 3-gram parameter values 2170 indicate that the level is active, with four indices and that the last index 2172 was three, corresponding to the last 3-gram 'sis'. The hash table 2180 has records of four 3-grams along with their corresponding index values. For convenience the matrix 2190 shows 'sis' 2192 where the corresponding index was determined in the fourth column and fourth row. Also in matrix 2190, the increment of number 2174 corresponds to one occurrence of the 4-gram 'ssis' as denoted at cell 2194.

Although no additional iterations are described in detail here, each additional iteration executes similarly. For each n-gram either a new index will be assigned or an old one will be reused. The remembered value of the last index L leads to an increment of the matrix, sometimes filling a zero space and sometimes increasing the count of certain n-grams. Occasionally the required indices will exceed the size of a matrix and this causes expansion of the matrix.

Figure 22A:
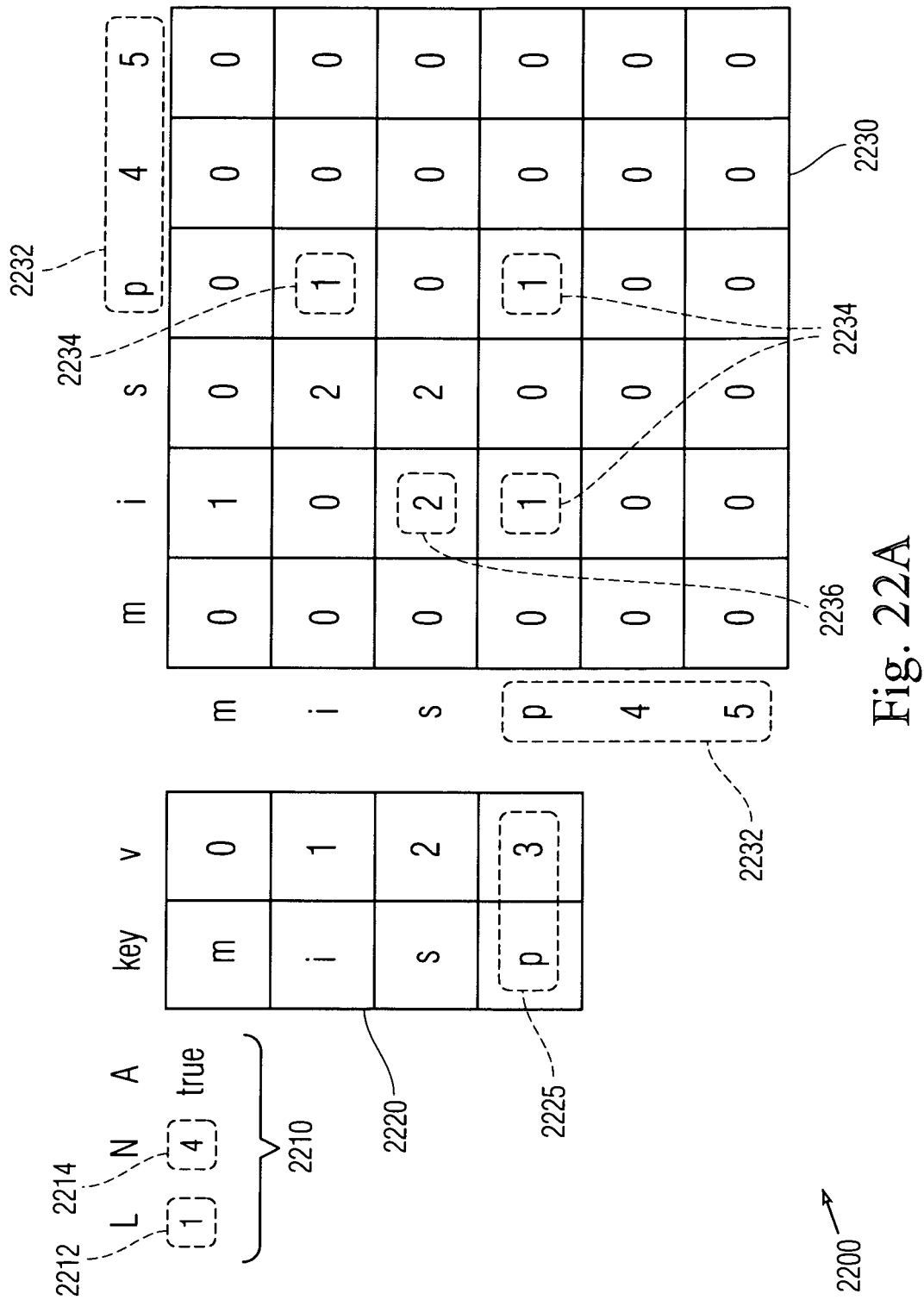
FIGS. 22A, 22B and 22C are tabular matrix views after completion of the final iteration.
Figure 22B:
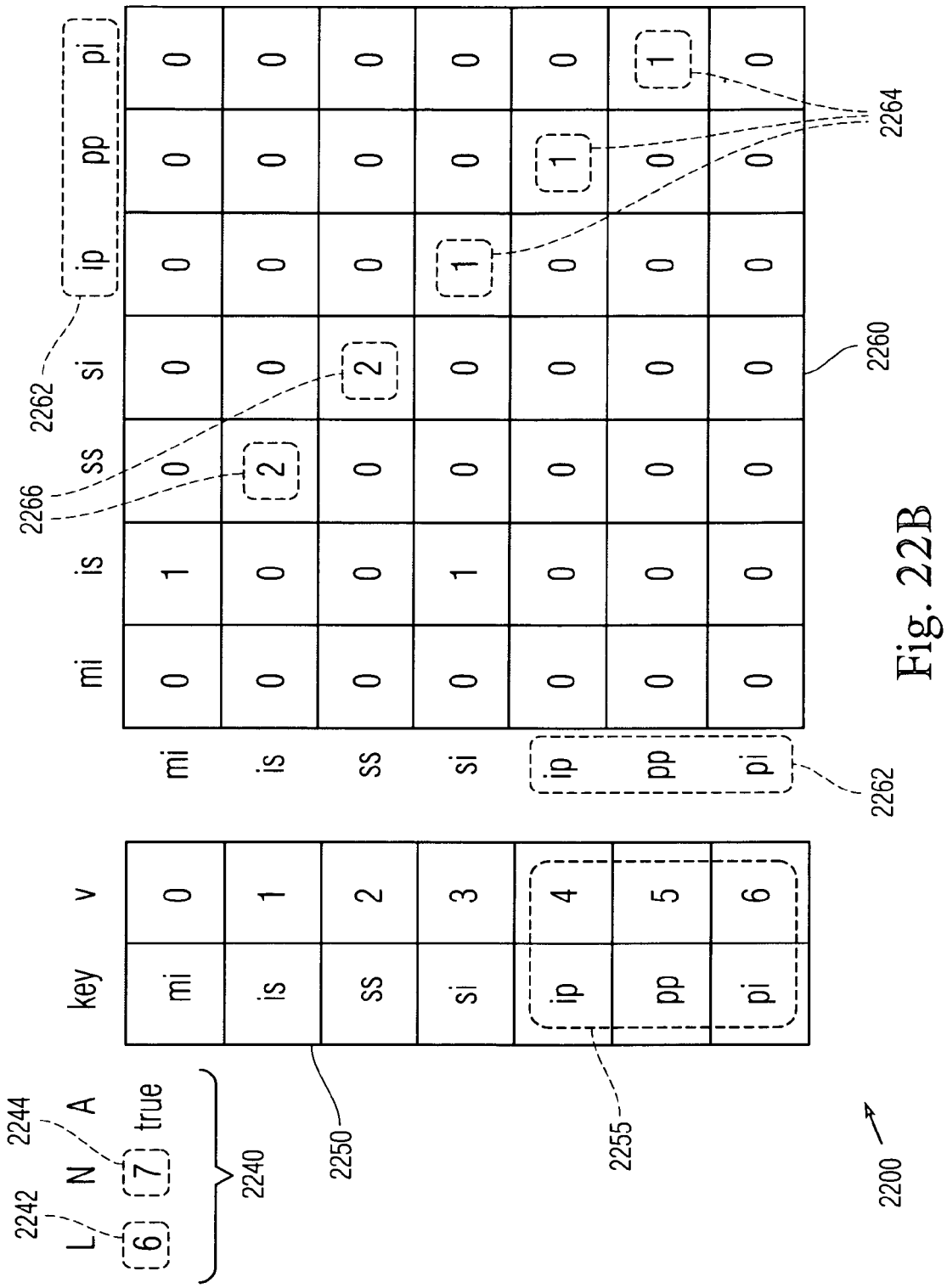
Figure 22C:
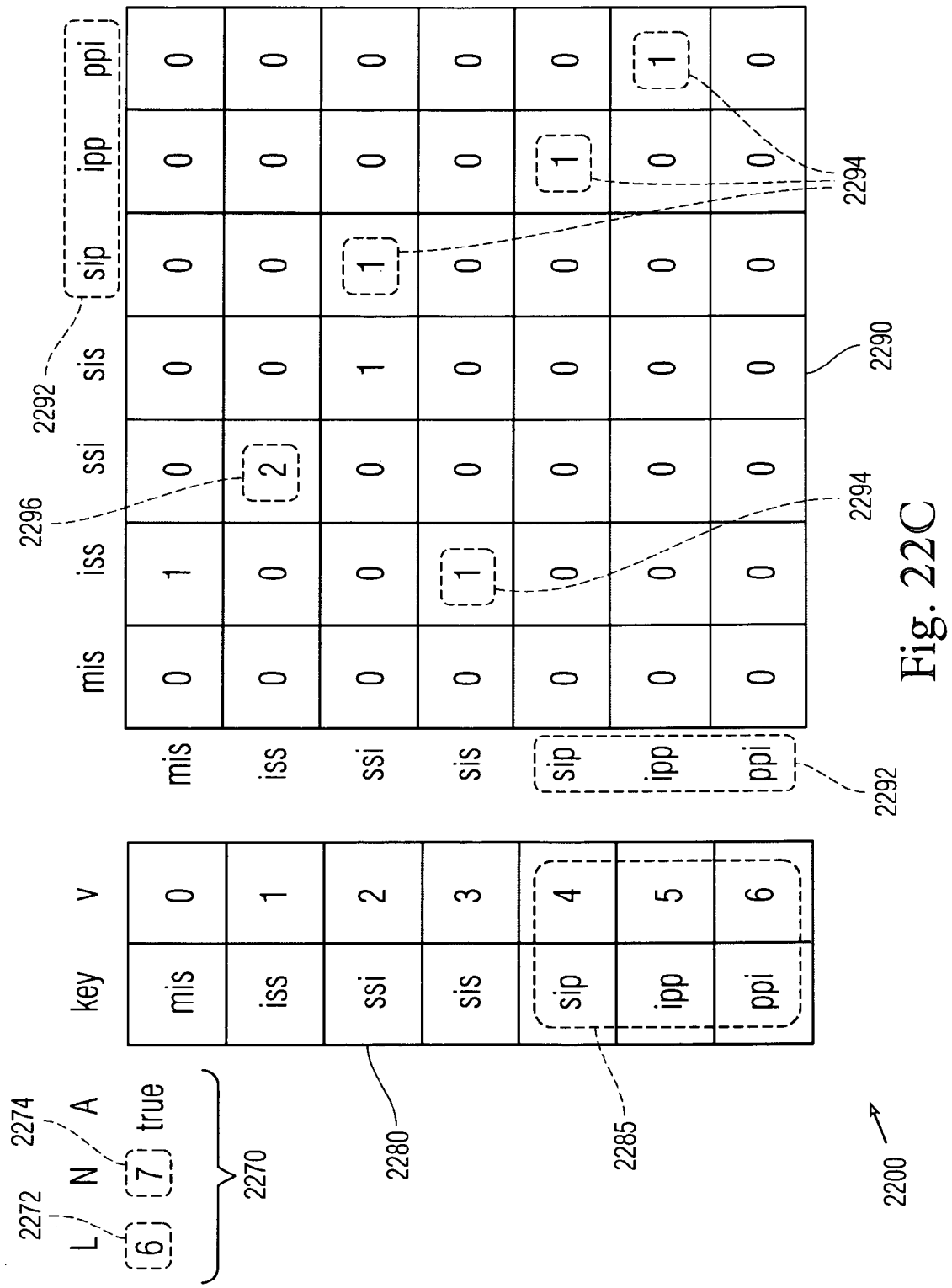

Final Iteration—Structure State: FIGS. 22A, 22B and 22C show tabular schematics 2200 of 1-gram, 2-gram and 3-gram graphs after process completion. FIG. 22A shows 1-gram parameter values 2210 with the last index 2212 reset to one (corresponding to the last letter 'i' in the sequence S), an increment of number N 2214 to four, a hash table 2220 with filled row 2225 denoting 1-gram 'p' and index four, and an expanded matrix 2230 with 'p 4 5' 2232 adding fourth through sixths rows and columns.

Occurrences of 'i' followed by 'p', of repeated 'p', and of 'p' followed by 'i' are indicated by value one in cells 2234 at the second row and fourth column and at the fourth row and second and fourth columns. Another occurrence of 's' followed by 'i' is indicated by value two in the cell 2236 at the third row and second column, incrementing the value from prior cell 2034 in that array position. FIG. 22B shows 2-gram parameter values 2240 with the last index 2242 set to six (corresponding to ending 2-gram 'pi'), an increment of number N 2244 to seven, and an expanded hash table 2250 with added rows 2255 denoting 2-grams 'ip', 'pp' and 'pi' and respective indices four through six.

FIG. 22B also shows an expanded matrix 2260 with entries 'ip pp pi' 2262 that replace the fifth and sixth rows and columns and add a seventh row and seventh column. The matrix 2260 shows 'ip pp pi' 2262 as corresponding to the fifth through seventh rows 2255 in the hash table 2250. Single occurrences of 'si' followed by 'ip', of 'ip' followed by 'pp' and of 'pp' followed by 'pi' are indicated by value one in cells 2264 at the fourth, fifth and sixth rows and respective fifth, sixth and seventh columns. Repeated occurrences of 'is' followed by 'ss' and of 'ss' followed by 'si' are indicated by value two in cells 2266 at the second and third rows and respective third and fourth columns, incrementing the value from respective prior cells 1964 and 2064 in those array positions.

FIG. 22C shows 3-gram parameter values 2270 with the last index 2272 set to six (corresponding to ending 3-gram 'ppi'), an increment of number N 2274 to seven, an expanded hash table 2280 with added rows 2285 denoting 3-grams 'sip', 'ipp' and 'ppi' with respective indices four through six, and an expanded matrix 2290 with 'sip ipp ppi' 2292 extending into the fifth through seventh rows and columns. The matrix 2290 shows 'sip ipp ppi' 2292 as corresponding to the fifth through seventh rows 2185 in the hash table 2280.

Single occurrences of 'ssi' followed by 'sip', of 'sis' followed by 'iss', of 'sip' followed by 'ipp' and of 'ipp' followed by 'ppi' correspond to respective occurrences of the 4-grams 'ssip', 'siss' 'sipp' and 'ippi' as indicated by the value one in cells 2294 at the third through sixth rows and respective fifth, second, sixth and seventh columns. Another occurrence of 'iss' followed by 'ssi' corresponds to a repeat occurrence 'issi' as indicated by the value two in cell 2296 at the second row and third column, incrementing the value from the prior cell 2094 in that array position.

Note that the 1-gram parameters 2210 indicate that there have been a total of four 1-grams and that the last one observed was at index one, corresponding to 'i'. The matrix 2230 has been enlarged since the sixth iteration, and one additional index value has been added corresponding to the 1-gram 'p'. Note that the 2-gram parameters 2240 indicate that there have been a total of seven 2-grams, and that the last one seen was at index six corresponding to 'pi'. Note that the 3-gram parameters 2270 indicate that there have been a total of seven 3-grams, and that the last such string was at index six corresponding to 'ppi'. The matrices 2260 and 2290 would have been expanded again to 12×12, but for convenience are shown here in the minimal form.

VI. Example Analysis:

Note that the sequence contains eleven values, but that the matrix of 1-grams 2230 indicates only ten values. This number actually corresponds to the number of 2-grams. With one exception, one can accurately give the frequency of 1-grams by a summation of each row. Thus in matrix 2230, the 1-gram 'm' appears only once (0+1+0+0+0+0) in the first row, while the 1-gram 's' appears four times (0+2+2+0+0+0) in the third row. Note the exception, that the summation indicates that the 1-gram 'i' appears only three times (0+0+2+1+0+0) in the second row. This superficial indication is incorrect. This off-by-one fault occurs on each hash table and corresponds to the last value shown. Thus this may be corrected for by referring to the index stored in last index L or for large values may be ignored. In this example the error introduces a significant variance (25%) for 1-grams, but in a larger example, that variance would be less significant.

Note also that there is a diagonal fill pattern in each matrix. This can be most readily seen in the third iteration where the matrix 1830 somewhat resembles the identity matrix and matrices 1860 and 1890 appear to be developing in a similar manner. However, even this short example demonstrates that by the last iteration 2230 is asymmetric and no longer subject to the diagonal fill. The same is true, but not as obvious for 2260 and 2290, which are nearly a diagonal fill, but with some aberration in the pattern. This suggests that there is a law of diminishing return for high-order n-gram hash tables.

The selection of a maximum n-gram size should be determined based on technical requirements of the application and the domain. For alphabets of size $\alpha$ the potential size of the matrix size is $\alpha^n$. As long as the sequence is larger than $\alpha^n$ the hash table will begin to deviate from the diagonal pattern. One may also consider that certain n-grams sequences are infeasible, further limiting that maximum matrix size. Obviously smaller alphabets and longer sequences may have significant data even at high orders of n, although deviation from the diagonal pattern may be seen earlier.

The exact nature of this diminishing return has not yet been studied by the inventors and to their knowledge has not been investigated in research literature. This is primarily because such analysis was infeasible under the old computing paradigm, being impossible using conventional state-of-the-art and de novo methods to examine the results of large order n-gram hash table for a large sequence.

The efficiency of storage for each matrix is related to this phenomenon. In this example the 6×6 matrix 2230 is 19% efficient and the 12×12 matrices 2260 and 2290 are each less than 5% efficient. Again, this example is a very small one, and one can observe that the smaller matrix is already becoming more efficient. For large order sequences that efficiency is likely to increase subject to the limitations discussed in Section II.

VII. Exemplary Code:

Exemplary executable code was produced from the pseudocode 1400. The only significant difference in both structure and algorithm was an additional hash table, which incorporated the index values as a key to find the corresponding text value. FIG. 23 shows tabular listings 2300 from an executable version of the process algorithm for the aforementioned sequence S (i.e., 'mississippi') to a parse degree of three. This analysis yields the lists of values in formatted arrays after completion of the final iteration. The first table 2310 shows the 1-gram result, analogous to matrix 2230. The second table 2320 shows the 2-gram result, analogous to matrix 2260. The third table 2330 shows the 3-gram result, analogous to matrix 2290.

VIII. Variants:

As noted in Section IV depending on the required output, the matrix may be relatively larger than the actual data. The parameter N in each case serves as an actual limit to the data size. Similar to the process described in the pseudocode 1400 at lines 24-27 a new matrix of the exact N×N dimensions may be created and the data may be copied into that matrix. In terms of the pseudocode 1400, such an action would occur after line 48. In terms of the flowchart 1300, such an action would occur just prior to Done 1395.

As noted in Section VII, the exemplary code added an addition hash table to the accompanying structure in order to map from indices to values. This alteration allowed the unification of two character sequences. For this domain this seemed a reasonable adaptation in order to execute the join method shown in psuedocode 1400 at line 44. Other similar adaptations may be necessary for other domains based on the concept of join in that domain. Such variants on the invention are to be expected and are idiosyncratic to the domain. They do not depart from the spirit of the embodiments.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A computer-implemented sequence analysis method for determining frequency in an n-gram sequence of a symbolic string, said method comprising:
    initializing a plurality of levels from one to n, such that operations for each level include:
    creating a hash table having first and second columns respectively assigned to a present value and a value index that corresponds to said present value;
    creating a matrix having first and second indices corresponding to an array of cells, said first index corresponding to an end of a prior value, said second index corresponding to a start of said present value;
    receiving said present value in the sequence;
    determining whether said present value is one of unknown and previously encountered;
    inserting said value index into said hash table for said present value being unknown, and identifying said value index in said hash table for said present value being encountered; and
    incrementing a cell within said array, said cell corresponding to said first index for said prior value and said second index for said present value.

2. The method according to claim 1, further including activating said level if previously inactive.

3. The method according to claim 1, further including expanding said hash table and said matrix in response to said present value being unknown said value index exceeding an insertion set in said hash table.

4. The method according to claim 1, further including updating a last level.

5. A computing platform that executes a sequence analysis process for determining frequency in an n-gram hash sequence of a symbolic string, said process comprising:
    a level initializer for initializing a plurality of levels from one to n, such that operations for each level include:
    a hash table generator for creating a hash table having first and second columns respectively assigned to a present value and a value index that corresponds to said present value;
    a matrix generator for creating a matrix having first and second indices corresponding to an array of cells, said first index corresponding to an end of a prior value, said second index corresponding to a start of said present value;
    an input device for reading said present value in the sequence;
    a determiner for determining whether said present value is one of unknown and previously encountered;
    a processor for inserting said value index into said hash table for said present value being unknown, and identifying said value index in said hash table for said present value being encountered; and
    a counter for incrementing a cell within said array, said cell corresponding to said first index for said prior value and said second index for said present value.

6. The process according to claim 5, further including an activator for activating said level if previously inactive.

7. The process according to claim 5, further including an expander for expanding said hash table and said matrix in response to said present value being unknown said value index exceeding an insertion set in said hash table.

8. The process according to claim 5, further including an updater for updating a last level.

* * * * *